(12) United States Patent
Nakayama et al.

(10) Patent No.: US 7,871,793 B2
(45) Date of Patent: Jan. 18, 2011

(54) ANTIMICROBIAL CARBOHYDRATES AND METHODS OF USING SAME

(75) Inventors: Jun Nakayama, Matsumoto (JP); Masatomo Kawakubo, Higashichikuma-Gun (JP); Minoru Fukuda, San Diego, CA (US); Tsutomu Katsuyama, Matsumoto (JP)

(73) Assignee: Burnham Institute for Medical Research, La Jolla, CA (US)

( * ) Notice: Subject to any disclaimer, the term of this patent is extended or adjusted under 35 U.S.C. 154(b) by 645 days.

(21) Appl. No.: 10/589,841

(22) PCT Filed: Feb. 18, 2005

(86) PCT No.: PCT/US2005/005407
§ 371 (c)(1),
(2), (4) Date: Jul. 5, 2007

(87) PCT Pub. No.: WO2005/081904
PCT Pub. Date: Sep. 9, 2005

(65) Prior Publication Data
US 2008/0026072 A1    Jan. 31, 2008

Related U.S. Application Data

(60) Provisional application No. 60/546,600, filed on Feb. 20, 2004.

(51) Int. Cl.
*C12P 21/06* (2006.01)
*C12P 21/00* (2006.01)

(52) U.S. Cl. ............................. 435/68.1; 800/4; 800/7

(58) Field of Classification Search ............... 435/68.1; 800/4, 7
See application file for complete search history.

(56) References Cited

U.S. PATENT DOCUMENTS
5,700,671 A    12/1997 Prieto et al.

FOREIGN PATENT DOCUMENTS
JP    2001 046077 A    2/2001

OTHER PUBLICATIONS

Nakayama et al. Expression Cloining of a Human alpha1, 4-N-Acetylglucosaminyltransferase that Forms GlcNA-calpha1->4Galbeta->R, a Glycan Speifically Expressing in the Gastric Gland Mucous Cell-Type Mucin. Proc. Natl. Acad. Sci, 1999, vol. 96, pp. 8991-8996.*

Nakayama et al., 1999, PNAS, vol. 96, pp. 8991-8996.*

Xing et al., 1989, Immunol. Cell Biol., vol. 67, pp. 183-195.*

Ashida et al., "A Novel Endo-Beta-Galactosidase from Clostridium Perfringens That Liberates the Disaccharide GlcNAcα1-4Gal from Glycans Specifically Expressed in the Gastric Gland Mucous Cell-type Mucin", *J. of Biological Chemistry* 276(30):28226-28232, 2001.

Nakayama et al., "Expression Cloning of a Human Alpha1,4-N-Acetylglucosaminyltransferase that Forms GlcNAc-Alpha-1,4-Gal-Beta-R, a Glycan Specifically Expressed in the Gastric Gland Mucous Cell-Type Mucin", *Proc. National Academy of Sciences*, 96(16):8991-8996, 1999.

Suzuki et al., "Molecular Cloning and Expression of a Novel Human Beta-Gal-3-O-Sulfotransferase that Acts Preferentially on N-Acetyllactosamine in N- and O-Glycans", *J. of Biological Chemistry*, 276(26):24388-24395, 2001.

Ujita et al., "Synthesis of Poly-N-Acetyllglucosamine in Core 2 Branched O-Glycans; The Requirement of Novel Beta-1, 4-Galactosyltransferase IV and Beta-1,3-N-Acetylglucosaminyltransferase", *J. of Biological Chemistry*, 273(52):34843-34849, 1998.

Zhang et al., "Immunohistochemical Demonstration of Alpha-1,4-N-Acetylglucosaminyltransferase that Forms GlcNAc-Alpha-1,4-Gal-beta Residues in Human Gastorintestinal Mucosa", *J. of Histochemistry and Cytochemistry*, 49(5):587-596, 2001.

Kawakubo et al., "Natural antibiotic function of a human gastric mucin against Helicobacter pylori infection", *Science*, 305(5686):1003-1006 (2004).

Kitagawa et al., "The tumor suppressor EXT-like gene EXTL2 encodes an alpha1, 4-N-acetylhexosaminyltransferase that transfers N-acetylgalactosamine and N-acetylglucosamine to the common glycosaminoglycan-protein linkage region. The key enzyme for the chain initiation of heparan sulfate", *J. Biol. Chem.*, 274(20):13933-13937 (1999).

Matsuzwa et al., "Helicobacter pylori infection up-regulates gland mucous cell-type mucins in gastric pyloric mucosa", *Helicobacter*, 8(6):594-600 (2003).

* cited by examiner

*Primary Examiner*—Peter Paras, Jr.
*Assistant Examiner*—David Montanari
(74) *Attorney, Agent, or Firm*—DLA Piper LLP (US)

(57) ABSTRACT

Compositions useful for inhibiting the growth of bacteria, including bacteria that can cause gastric ulcers, are provided. In addition, transgenic organism that can produce such compositions are provided. Methods of using the compositions to treat or prevent gastric ulcers in a subject, including a human subject, also are provided.

3 Claims, 5 Drawing Sheets

ANTIMICROBIAL CARBOHYDRATES AND METHODS OF USING SAME

CROSS REFERENCE TO RELATED APPLICATIONS

This application is a 35 USC §371 National Stage application of PCT Application No. PCT/US2005/005407 filed Feb. 18, 2005; which claims the benefit under 35 USC §119(e) to U.S. Application Ser. No. 60/546,600 filed Feb. 20, 2004, now abandoned. The disclosure of each of the prior applications is considered part of and is incorporated by reference in the disclosure of this application.

GRANT INFORMATION

This invention was made with government support under Grant Nos. CA 71932 and CA 33000 awarded by the National Cancer Institute. The United States government has certain rights in this invention.

BACKGROUND OF THE INVENTION

1. Field of the Invention

The invention relates generally to antimicrobial compositions, and more specifically to O-glycans containing terminal α1,4-linked N-acetylglucosamine residues, compositions containing such terminal α1,4-linked N-acetylglucosamine residues, and methods of using the compositions to prevent and/or treat bacterial infections.

2. Background Information

The stomach provides a very acidic environment that aids in the digestion of food, thus freeing up nutrients can be absorbed through the intestine. Generally, the cells lining the stomach are protected by a mucus layer, which is produced by cells of the stomach. Stomach ulcers (gastric ulcers) occur when a region of the stomach is exposed to the acid environment, thus resulting in the formation of a raw area or open sore in the lining of the stomach.

Stomach ulcers can occur due to increased production of acid in the stomach or by ingestion of acidic materials, and commonly occur in individuals who take non-steroid anti-inflammatory drugs (NSAIDs) such as aspirin and ibuprofen, or drink too much alcohol or caffeine. About 70% of patients with gastric ulcers are infected with *Helicobacter pylori* (*H. pylori*). Most gastric ulcers that are not related to treatment with NSAIDs are accompanied by antral gastritis and *H. pylori* infection, whereas about 50% of gastric ulcers associated with these medications are not accompanied by *H. pylori*-associated gastritis. If patients with ulcers induced by NSAIDs are excluded, the prevalence of infection with *H. pylori* in patients with gastric ulcers is about 96%.

*Helicobacter pylori* is a microaerobic, gram negative and rod-shaped bacterium (bacillus) which lives on the lining of the stomach of about half the people on earth. It is considered to be a major cause of gastritis, chronic gastritis, gastric ulcer and duodenal ulcer. A relationship between *Helicobacter pylori* and diseases such as gastric cancer has also been reported. Development of a remedy for diseases caused by *Helicobacter pylori* is an important theme for maintaining health and well-being.

Antibiotics such as penicillin, tetracycline, cephalosporin and neuroquinone are known to be anti-*Helicobacter pylori* agents. However, although they exhibit antibacterial action against *Helicobacter pylori*, single administration of these agents is not sufficient to kill the bacteria. Recently, triple therapy has mainly been conducted using these antibiotics together with a bismuth agent and proton pump inhibitor. In addition, an anti-*Helicobacter pylori* agent containing benzohydroxamic acid has been proposed (Japanese Patent Application Laid-Open (JP-A) No. 11-189529). It is, however, inferior from the point of view of safety, because side effects such as diarrhea and vomiting can result.

An anti-*Helicobacter pylori* agent containing steryl glucopyranoside extracted from plants has also been proposed (JP-A No. 2003-73278). Further, an anti-*Helicobacter pylori* agent containing a component extracted from crude drugs such as Coptidis Rhizoma and a hydrogen carbonate of an alkali metal has been proposed (JP-A No. 2002-370995). However, these agents have side effects because they are not produced in the human living body and moreover, their antibacterial effects against *Helicobacter pylori* are insufficient. None of the above-described proposals includes disclosure about deterioration in the motility and abnormal morphology of *Helicobacter pylori*.

The goal of treatment for gastric ulcers include pain relief, healing of the ulcer, prevention of complications, and prevention of recurrence of the ulcer. Complications due to untreated ulcers can include hemorrhage, perforation of the stomach wall, and obstruction due to scarring. In addition, about 2-3% of patients with stomach ulcers develop stomach cancer. Antibiotics are used to treat gastric ulcer patients infected with *H. pylori*. Treatment with antibiotics allows the ulcer to heal after the *H. pylori* infection is cured, and, if the treatment is successful, less than 5% of patients have a recurrence over the next year (as compared to a 60 to 80% recurrence rate if *H. pylori* infection is not cured).

*H. pylori* are difficult to eradicate from the stomach because the bacteria live deep in the mucous layer that covers the lining of the stomach, and it is difficult for antibiotics to penetrate into this mucous layer in sufficient concentrations to kill the bacteria. Generally, treatment with a single drug is ineffective in eliminating *H. pylori* infection. For example, amoxicillin has an eradication rate of less than 20%, and metronidazole has an eradication rate of less than 10%, while treatment with clarithromycin has an eradication rate of about 40%. As such, combination therapies are used, including combinations of two drugs (e.g., two antibiotics, or one antibiotic and one acid-lowering drug), and combinations of three drugs (e.g., two antibiotics and one acid-lowering drug). Eradication rates using a combination of two antibiotics range from 40% to 60%, and the best combinations of three drugs currently provide greater than 90% eradication of *H. pylori* infection in treated patients.

Unfortunately, *H. pylori*, like other bacteria, can become resistant to antibiotics, thus lowering the success rate of treatment. For example, resistance to metronidazole has been reported to be as high as 40% in some regions; and resistance to clarithromycin has been reported, though at a very low frequency (less than 2%). Since antibiotic resistance generally increases with time, there is concern that they may become progressively less effective for eradicating *H. pylori* and treating gastric ulcers. However, substances having sufficient antibacterial effects, being free from side effects, and having excellent safety, and their application technique have not yet been proposed. Thus, a need exists for compositions and methods of preventing and treating gastric ulcers.

SUMMARY OF THE INVENTION

The present invention is based on the discovery that gastric gland mucous cell-type mucins, including mucins containing terminal α1,4-linked N-acetylglucosamine (α1,4-linked GlcNAc) residues, can inhibit the growth of *Helicobacter*

*pylori* (*H. pylori*), which can infect the stomach and cause gastric ulcers. Based on the identification of this activity of gastric gland mucous cell-type mucins, exemplary glycoproteins containing α1,4-linked GlcNAc) residues were prepared and were shown effectively inhibit cholesteryl-α-D-glucopyranoside synthesis and growth of *H. pylori*. Accordingly, the present invention provides substances that can be used suitably for any one of remedies for gastric ulcer, remedies for duodenal ulcer, anti-*H. pylori* agents, remedies for gastritis, and drugs for alleviating chronic gastritis; processes for producing the substances; processes for treating gastric ulcer by using the substances; and transgenic mammals capable of producing the substances.

The present invention relates to a non-naturally occurring compound, which includes at least one terminal α1,4-linked N-acetylglucosamine (α1,4-linked GlcNAc) residue operatively linked to a carrier molecule. The carrier molecule can be any molecule to which one or more α1,4-linked GlcNAc residues can be linked, including, for example, an O-glycan (e.g., a core2-branched O-glycan), a polypeptide, particularly a polypeptide containing at least one O-glycosylation site, or a glycoprotein (e.g., a polypeptide containing one ore more O-glycans, for example, a polypeptide containing a core2-branched O-glycan). In one aspect, the carrier molecule is a mucin-like polypeptide, for example, CD43 (leukosialin) or CD34. In another aspect, the compound contains a plurality of α1,4-linked GlcNAc residues, for example, 2, 3, 4, 5, or more α1,4-linked GlcNAc residues. In still another aspect, the compound is a synthetic oligosaccharide.

The present invention also relates to a method of producing a glycoprotein containing at least one α1,4-linked GlcNAc residue. Such a method can be performed, for example, by contacting, under conditions suitable for glycosylation of a polypeptide, an α1,4-N-acetylglucosaminyl transferase (α4GnT), a core2β1,6-N-acetylglucosaminyl transferase-I (C2GnT-I), or a core 1 extension enzyme (e.g., a core1 extension β1,3-N-acetylglucosaminyl transferase; "core1-β3GlcNAcT" or "C1-β3GnT") and a carrier polypeptide, which contains at least one O-glycosylation site, whereby the carrier polypeptide is glycosylated by the C2GnT-I or by the C1-β3GnT, and the α4GnT, thereby producing a glycoprotein containing at least one α1,4-linked GlcNAc residue. The carrier polypeptide can be any polypeptide to which one or more α1,4-linked GlcNAc residues can be attached due to the activity of C2GnT-I (or of C1-β3GnT) and α4GnT, including, for example, a soluble polypeptide (e.g., a soluble CD43 or CD34 polypeptide).

In one embodiment, the carrier polypeptide comprises mucin-type glycoproteins that normally are present in milk of a mammal. In one aspect of this embodiment, the method is performed in vitro by contacting milk of the mammal with at least an α4GnT and, optionally, a C2GnT-I and/or C1-β3GnT, whereby mucin-type glycoproteins of the milk are modified to contain at least one α1,4-linked GlcNAc residue. In another aspect of this embodiment, the mucin-type glycoproteins are isolated from the milk of the mammal, and the method is performed by contacting mucin-type glycoproteins isolated from the milk with at least an α4GnT and, optionally, a C2GnT-I and/or C1-β3GnT, whereby the mucin-type glycoproteins of the milk are modified to contain at least one α1,4-linked GlcNAc residue.

A method of producing a glycoprotein containing at least one α1,4-linked GlcNAc residue can further include a step of isolating the glycoprotein. As such, a glycoprotein containing at least one α1,4-linked GlcNAc residue produced by a method of the invention is provided, as is an isolated glycoprotein produced by such a method.

The present invention further relates to a method of producing a recombinant glycoprotein containing at least one α1,4-linked GlcNAc residue. Such a method can be performed, for example, by expressing in a eukaryotic cell, at least a polynucleotide encoding a heterologous α4GnT, whereby a polypeptide, which can be an endogenous polypeptide produced by the cell, is glycosylated by the α4GnT and a C2GnT-I (or by a C1-β3GnT) expressed in the cell. For example, a mammary cell expresses endogenous C2GnT-I and polypeptides that can be glycosylated such that, in the presence of an expressed exogenous (heterologous) α4GnT, a recombinant glycoprotein containing at least one α1,4-linked GlcNAc residue is produced. It should be noted that, in such a case, the glycoprotein is considered a "recombinant" glycoprotein because it is not naturally modified to contain a α1,4-linked GlcNAc residue in the eukaryotic cell, but is produced only due to expression of the heterologous α4GnT in the cell. In another aspect, a polynucleotide encoding a heterologous C2GnT-I and/or a polynucleotide encoding a heterologous carrier polypeptide comprising at least one O-glycosylation site, is expressed in the cell, depending, for example, on whether the eukaryotic cell naturally expresses an endogenous C2GnT-I or the desired carrier polypeptide, whereby the carrier polypeptide is glycosylated by the C2GnT-I, which may be an endogenous or exogenous (heterologous) C2GnT-I, and the α4GnT.

The carrier polypeptide can be a soluble polypeptide, for example, a soluble CD43 or a soluble CD34, and the recombinant glycoprotein can contain one or a plurality of α1,4-linked GlcNAc residues. The eukaryotic cell can be any eukaryotic cell in which the encoding polynucleotides can be expressed, and in which either an endogenous C2GnT-I a heterologous C2GnT-I and the heterologous α4GnT have enzymatic activity such that one or more α1,4-linked GlcNAc residues can be linked to the carrier polypeptide, which can be an endogenous carrier polypeptide or a heterologous carrier polypeptide. For example, the eukaryotic cell can be a mammalian cell such as a Chinese hamster ovary cell or a human cell such as a mammary epithelial cell. In addition, the method can further include a step of isolating the recombinant glycoprotein. As such, a recombinant glycoprotein, including an isolated recombinant glycoprotein, produced by the method of the invention is provided.

The present invention also relates to a non-human transgenic mammal, which contains, stably integrated in its genome, at least a first exogenous polynucleotide encoding α4GnT, and further contains a polynucleotide encoding C2GnT-I and a polynucleotide encoding a carrier polypeptide, wherein the first exogenous polynucleotide is operatively linked to a 5' regulatory sequence that directs expression of the encoded C2GnT in cell or cell of interest. As such, the 5' regulatory sequence can be a constitutively active promoter, inducible promoter, tissue-specific promoter, or the like. In one embodiment, the 5' regulatory sequence comprises a mammary gland specific promoter, in which case the polynucleotides encoding the C2GnT-I and carrier polypeptide can, but need not, be endogenous polynucleotides (i.e., genes contained in the genome of the non-human animal). In a second embodiment, the polynucleotide encoding C2GnT-I is a second exogenous polynucleotide encoding C2GnT-I; and/or the polynucleotide encoding the carrier polypeptide is a third exogenous polynucleotide encoding a carrier polypeptide comprising at least one O-glycosylation site. In one aspect of this embodiment, each of the first exogenous polynucleotide, second exogenous polynucleotide (when present), and third exogenous polynucleotide (when present) is operatively linked to a 5' regulatory sequence of a mammary gland-specific gene including a promoter. In a further aspect of this embodiment, the third exogenous polynucleotide (when present) is operatively linked to a nucleotide sequence encoding a signal sequence effective in directing secretion of the carrier polypeptide into milk. Upon expression of the C2GnT-I, α4GnT, and carrier polypeptide in such a transgenic mammal of the invention, the carrier polypeptide is glycosylated by the C2GnT-I and the α4GnT, thereby producing a recombinant glycoprotein containing at least one α1,4-linked GlcNAc residue.

A promoter, which can comprise all or a portion of a 5' regulatory sequence of a mammary gland-specific gene, useful for purposes of the present invention, can be any promoter that provides mammary gland specific expression. Such promoters are exemplified by a whey acidic protein promoter, an α-casein promoter, a β-casein promoter, a κ-casein promoter, an α-lactalbumin promoter, and a β-lactoglobulin promoter. The first exogenous polynucleotide, second exogenous polynucleotide, and third exogenous polynucleotide further can be operatively linked to 3' regulatory sequences from a mammary gland-specific gene or 3' regulatory sequences active in a mammary gland.

A non-human transgenic mammal of the invention can be prepared using one, two, or three transgenes. Thus, in one aspect, each of the first exogenous polynucleotide, second exogenous polynucleotide, and third exogenous polynucleotide independently can be operatively linked to a 5' regulatory sequence and, optionally, a 3' regulatory sequence, as indicated. In another aspect, the first exogenous polynucleotide, second exogenous polynucleotide, and third exogenous polynucleotide are operatively linked to each other to form a single transgene that is further operatively linked to a 5' regulatory sequence and, optionally, a 3' regulatory sequence, as indicated. In other aspects, two transgenes are provided, for example, a first transgene comprising the first exogenous polynucleotide operatively linked to the second exogenous polynucleotide, and a second transgene comprising the third exogenous polynucleotide, wherein each of the first and second transgene is further operatively linked to a 5' regulatory sequence and, optionally, a 3' regulatory sequence, as indicated.

A non-human transgenic mammal of the invention can be any mammal, including, for example, a mouse, a rat, a rabbit, a horse, a pig, a sheep, a goat, or a cow. In one embodiment, the transgenic mammal is a female non-human transgenic mammal, in which the recombinant glycoprotein can be secreted in an antimicrobially active form into milk produced by the female nonhuman transgenic mammal. Accordingly, milk produced by such a female non-human transgenic mammal also is provided.

The present invention further relates to a method for producing an antimicrobial recombinant glycoprotein containing at least one α1,4-linked GlcNAc residue in milk of a female non-human transgenic mammal. Such a method can be performed, for example, by introducing into a non-human mammalian embryo a first exogenous polynucleotide encoding α4GnT; optionally, a second exogenous polynucleotide encoding C2GnT-I) or a corel extension β1,3-N-acetylglucosaminyl transferase (C1-β3GnT); and/or optionally, a third exogenous polynucleotide encoding a carrier polypeptide comprising at least one O-glycosylation site, wherein the first exogenous polynucleotide, the second exogenous polynucleotide (when present), and the third exogenous polynucleotide (when present) are operatively linked to a 5' regulatory sequence of a mammary gland-specific gene including a promoter; and wherein the third exogenous polynucleotide (when present) is operatively linked to a nucleotide sequence encoding a signal sequence effective in directing secretion of the carrier polypeptide into milk; transferring the embryo thereby into a recipient female mammal such that progeny are produced; inducing milk production in a resulting female progeny containing the first exogenous polynucleotide, second exogenous polynucleotide, and third exogenous polynucleotide operatively linked to the 5' regulatory sequence stably integrated its genome. Upon expression of the C2GnT-I, α4GnT, and carrier polypeptide in a female non-human transgenic mammal generated according to such a method, the carrier polypeptide is glycosylated by the C2GnT-I (or by the C1-β3GnT) and the α4GnT, thereby producing an antimicrobial recombinant glycoprotein comprising at least one α1,4-linked GlcNAc residue, which is secreted into the milk of the female non-human transgenic mammal.

Such a method of producing a female non-human transgenic mammal can further include a step of milking the female progeny, thereby obtaining milk containing the recombinant glycoprotein comprising at least one α1,4-linked GlcNAc residue. Further, the method can include isolating the recombinant glycoprotein comprising at least one α1,4-linked GlcNAc residue from the milk, thereby obtaining the recombinant glycoprotein comprising at least one α1,4-linked GlcNAc residue. Accordingly, the invention provides a female non-human transgenic mammal produced by such a method, milk produced from such a female transgenic mammal, and an isolated recombinant glycoprotein comprising at least one α1,4-linked GlcNAc residue obtained by the method.

The present invention also relates to a method of reducing or inhibiting cell wall formation of a bacterium that expresses cholesteryl-α-D-glucopyranoside (CGL). Such a method can be performed, for example, by contacting the bacterium with a compound containing at least one α1,4-linked GlcNAc residue, whereby CGL synthesis is reduced or inhibited, thereby reducing or inhibiting cell wall formation of the bacterium. In one aspect, the compound reduces or inhibits UDP-Glc:sterol glucosyltranserase activity in the bacterium, thereby reducing or inhibiting CGL synthesis. The bacterium can be any bacterium that expresses GGL, including a *Helicobacter* species, particularly *H. pylori*. The compound can be a compound of the invention, including, for example, a recombinant glycoprotein of the invention, or can be a gastric gland mucous cell-type mucin isolated from gastric gland mucosal cells.

In addition, the invention relates to a method of reducing or inhibiting growth of bacteria expressing CGL. Such a method can be performed, for example, by contacting the bacteria with a compound containing at least one α1,4-linked GlcNAc, whereby CGL synthesis is reduced or inhibited, thereby reducing or inhibiting growth of the bacterium. The method can be performed by contacting the bacteria in vitro, for example, by adding the compound to bacteria cells in culture, or by contacting the bacteria in vivo, for example, by directing the compound to the stomach of a subject infected with the bacteria, for example, a mammal infected with a *Helicobacter* species (e.g., a human infected with *H. pylori*). The compound can be any compound containing at least one α1,4-linked GlcNAc, for example, an O-glycan, which can be obtained using a method as disclosed herein, or can be a gastric gland mucous cell-type mucin isolated from gastric gland mucosal cells.

The present invention further relates to methods of treating or preventing gastric ulcers due to infection with a *Helicobacter* species. Accordingly, in one embodiment, the invention provides a method of ameliorating signs or symptoms of a gastric ulcer due to a *Helicobacter* species infection in a subject. Such a method can be performed, for example, by administering to the subject a compound containing at least one α1,4-linked GlcNAc residue, whereby the compound, upon contacting the *Helicobacter*, reduces or inhibits growth of the *Helicobacter* species, thereby ameliorating signs or symptoms of the gastric ulcer and/or gastric cancer.

In another embodiment, the invention provides a method of preventing gastric ulcers due to a *Helicobacter* infection in a subject susceptible to such gastric ulcers. Such a method can be performed, for example, administering to the susceptible subject, a compound containing at least one α1,4-linked GlcNAc residue, whereby the compound prevents *Helicobacter* growth, thereby preventing the formation of gastric ulcers due to the *Helicobacter* species.

In yet another embodiment, the invention relates to a method of ameliorating gastric ulcers or gastric cancer due to infection by a *Helicobacter* species in a subject having gastric ulcers or gastric cancer by administering to the subject a compound comprising at least one α1,4-linked GlcNAc residue, whereby the compound prevents *Helicobacter* growth, thereby ameliorating gastric ulcers or gastric cancer due to infection by the *Helicobacter*. For example, the method can include the subject drinking milk containing the compound, wherein the milk is obtained from a transgenic non-human mammal as disclosed herein.

A subject treated according to a method of the invention can be any subject having or susceptible to having a *Helicobacter* infection in the gastric mucosa. Thus, the subject can be, for example, a mammalian subject, which can be a horse, a pig, a goat, a dog, a cat, a ferret, or the like. In one embodiment, the subject is a human. Correspondingly, the *Helicobacter* species can be any species implicated in the formation of gastric ulcers, including, for example, *H. pylori*, which is implicated in the formation of gastric ulcers in humans.

The compound can be any compound containing at least one terminal α1,4-linked GlcNAc residue, which, as disclosed herein, can reduce or inhibit the growth of a *Helicobacter* species. Thus, the compound can be a synthetic oligosaccharide, a recombinant glycoprotein containing one or more α1,4-linked GlcNAc residues (e.g., a soluble CD43 polypeptide containing terminal α1,4-linked GlcNAc residues), a compound comprising an O-glycan, which contains one or more terminal α1,4-linked GlcNAc residues, or a compound containing gastric gland mucous cell-type mucin, which can be isolated from gastric gland mucosal cells. Methods for making such compounds containing at least one terminal α1,4-linked GlcNAc residue are routine and well known in the art. For example, methods of making a synthetic oligosaccharide useful as a carrier molecule include methods of making a core2 oligosaccharide (see, e.g., Sengupta et al., *Tetrahedron Lett.* 44:6037-6042, 2003; Ong et al., *J. Biol. Chem.* 277;18182-18190, 2002, each of which is incorporated herein by reference), methods of making an extended corel oligosaccharide (see, e.g., Belot et al., *Tetrahedron Lett.* 74:2-6, 2002, which is incorporated herein by reference), and methods of adding an α1,4-GlcNAc to core2 branched O-glycans (see, e.g., Nakayama et al., *Proc. Natl. Acad. Sci., USA* 96;8991-8996, 1999, which is incorporated herein by reference). Further, the compound can be administered in any convenient way, particularly orally such that it is directed to the stomach. In one aspect, administration is performed by the subject having or susceptible to having gastric ulcers due to *Helicobacter* infection drinking milk containing the compound, for example, milk from a female non-human transgenic mammal of the invention.

The present invention also relates to a transgenic plant containing, stably integrated in its genome, at least first exogenous polynucleotide encoding an (α4GnT; a second polynucleotide encoding a C2GnT-I or encoding a C1-β3GnT; and a third polynucleotide encoding a carrier polypeptide comprising at least one O-glycosylation site, wherein at least one of the first polynucleotide, second polynucleotide, and third polynucleotide is an exogenous polynucleotide; and wherein the first polynucleotide, second polynucleotide, and third polynucleotide are operatively linked to a plant gene 5' regulatory sequence, including a promoter; and whereby, upon expression of the C2GnT-I or the C1-β3GnT, the α4GnT, and the carrier polypeptide, the carrier polypeptide is glycosylated by the C2GnT-I or by the C1-β3GnT, and the α4GnT, thereby producing a recombinant glycoprotein comprising at least one α1,4-linked GlcNAc residue. In such a transgenic plant, at least one of second polynucleotide and/or the third polynucleotide also can be an exogenous polynucleotide, and, in one embodiment, each of the first polynucleotide, second polynucleotide, and third polynucleotide is an exogenous polynucleotide.

A promoter operatively linked to an exogenous nucleic acid molecule in a transgenic plant of the invention can be a constitutive promoter, an inducible promoter, or a tissue specific promoter, provided that the promoter directs transcription of the encoded polypeptide (e.g., α4GnT) in the desired cells of the plants, including, for example, in seeds, flowers, leaves, and/or roots. For example, the promoter can be a constitutively active 35S cauliflower mosaic virus promoter, ubiquitin promoter, or rice actin promoter, an inducible tetracycline responsive promoter or rbcS gene light inducible promoter, or a seed specific oleosin gene promoter.

A transgenic plant of the invention can be any plant, including monocots or dicots and gymnosperms or angiosperms. Further, the transgenic plant can be one that is used as source of food for humans or animals, or that is useful commercially, for example, for agricultural "pharming" (i.e., for producing a genetically engineered product). Thus, the transgenic plant can be, for example, a soybean plant, rice plant, corn (maize) plant, or wheat plant. Accordingly, the invention provides, for example, seeds produced by such a transgenic plant; products such as grain produced from such a transgenic plant; and products derived from seeds, grain, and the like, for example, a milk product such as soymilk or rice milk.

The present invention also relates to a method for producing an antimicrobial recombinant glycoprotein comprising at least one α1,4-linked GlcNAc residue in a transgenic plant. Such a method can be performed, for example, by introducing into a plant cell at least a first exogenous polynucleotide encoding an α4GnT, wherein the first exogenous polynucleotide is operatively linked to a 5' regulatory sequence of a plant gene, including a promoter, and whereby, upon expression of the α4GnT, a carrier polypeptide in cells of the plant is glycosylated by the α4GnT, thereby producing an antimicrobial recombinant glycoprotein comprising at least one α1,4-linked GlcNAc residue; and growing a plant from the plant cell containing the introduced exogenous nucleic acid molecule, thereby obtaining a transgenic plant, whereby an antimicrobial recombinant glycoprotein comprising at least one α1,4-linked GlcNAc residue is produced in the transgenic plant. Such a method can further include introducing into the plant cell a second exogenous polynucleotide encoding an exogenous C2GnT-I or encoding an exogenous C1-β3GnT; and/or a third exogenous polynucleotide encoding an exogenous carrier polypeptide comprising at least one O-glycosylation site, wherein the second exogenous polynucleotide, when present, and the third exogenous polynucleotide, when present, is operatively linked to a 5' regulatory sequence of a plant gene, including a promoter; and whereby, upon expression of the C2GnT-I or the C1-β3GnT, when present, the α4GnT, and the exogenous carrier polypeptide, when present, the carrier polypeptide is glycosylated by the C2GnT-I or by the C1-β3GnT, when present, and the α4GnT, thereby producing an antimicrobial recombinant glycoprotein comprising at least one α1,4-linked GlcNAc residue in the transgenic plant.

A method for producing an antimicrobial recombinant glycoprotein comprising at least one α1,4-linked GlcNAc residue in a transgenic plant can further include isolating a transgenic plant product from the transgenic plant, including, for example, seeds, leaves, roots, and/or flowers from the transgenic plant. In addition, the method can further include isolating the recombinant glycoprotein comprising at least one α1,4-linked GlcNAc residue from the transgenic plant or the transgenic plant product. In one embodiment, the method further includes processing the transgenic plant or transgenic plant product to obtain a milk product that contains the recombinant glycoprotein comprising at least one α1,4-linked GlcNAc residue. Accordingly, an isolated recombinant glycoprotein comprising at least one α1,4-linked GlcNAc residue produced by a method of the invention, a transgenic plant product produced by a method of the invention, and milk obtained by a method of the invention also are provided.

BRIEF DESCRIPTION OF THE DRAWINGS

FIG. 2A provides a growth curve of *H. pylori* incubated with soluble CD43 with terminal α1,4-linked GlcNAc (αGlcNAc (+)) or soluble CD43 without terminal α1,4-linked GlcNAc (lGlcNAc (−)). One milli-unit (mU) of αGlcNAc (+) is defined as an immunoreactivity equivalent to 1 Tg of p-nitrophenyl-N-acetyl-α-glucosamine (GlcNAcα-PNP). Protein concentration of αGlcNAc (−) was the same as that of 125.0 mU/ml of αGlcNAc (+).

FIG. 2B shows the motility of *H. pylori* cultured with 31.2 mU/ml of soluble CD43 with terminal α1,4-linked GlcNAc (αGlcNAc (+)) or the same protein concentration of soluble CD43 without terminal α1,4-linked GlcNAc (αGlcNAc (−)) for 3 days by time-lapse recording with 1 sec-intervals. Representative *H. pylori* are indicated by arrowheads. The mean velocity of seven *H. pylori* cultured in the presence of αGlcNAc (+) and αGlcNAc (−) is 3.1±3.5 μm/sec (mean±SD) and 21.2±2.6 μm/sec, respectively, with a statistical significance of P<0.001 (Student's t test). Bar=50 μm.

FIG. 2C shows scanning electron micrographs of *H. pylori* incubated with 31.2 mU/ml of soluble CD43 with terminal α1,4-linked GlcNAc (αGlcNAc (+)) or the same protein concentration of soluble CD43 without terminal α1,4-linked GlcNAc (αGlcNAc (−)) for 3 days. Note abnormal morphologies such as elongation, segmental narrowing, and curving in the culture with αGlcNAc (+). All photographs are taken at the same magnification, and the bar indicates 1 Tm.

FIG. 3A shows that sodium-adducted CGL, {M+Na}$^+$ at m/z 571.6, is detected in the lipid fraction of *H. pylori* incubated with soluble CD43 without terminal α1,4-linked GlcNAc residues (arrow).

FIG. 3B provides a similar analysis of CGL on samples cultured with 4.0 mU/ml of soluble CD43 with terminal α1,4-linked GlcNAc residues. Note that the relative amounts of CGL to phosphatidic acid, which serves as an internal standard (Inamoto et al., *J. Clin. Gastroenterol.* 17:S136, 1993, which is incorporated herein by reference), are significantly reduced to 29.5% of the control experiment (FIG. 2A; see arrow). Mean value of duplicate experiments is shown.

FIG. 3C shows a MALDI-TOF mass spectrum of products synthesized from UDP-Glc and cholesterol by somicated *H. pylori*. CGL {M+Na}$^+$ at m/z 571.6 is shown.

FIG. 3D shows a mass spectrum of products synthesized from UDP-Glc and cholesterol by sonicated *H. pylori* in the presence of 50.0 mU/ml of soluble CD43 with terminal α1,4-linked GlcNAc. Note that a peak for CGL is not detectable under this condition.

FIG. 3E shows a mass spectrum of products synthesized from UDP-Glc and cholesterol by sonicated *H. pylori* in the presence of soluble CD43 without terminal α1,4-linked GlcNAc. Note that CGL is synthesized under this condition.

DETAILED DESCRIPTION OF THE INVENTION

Compositions and methods are provided that are useful, for example, for preventing and treating gastric ulcers due to infection with a *Helicobacter* species such as *H. pylori*, which can cause gastric ulcers in humans. Accordingly, the present invention provides molecules, functional molecules, compositions, pharmaceuticals, foods, beverages, and milk that possess antibacterial activity, including inhibiting growth and motility and causing abnormal morphology, against *Helicobacter* genus bacteria, wherein the antibacterial activity against *Helicobacter* genus bacteria is selective and specific, thereby being free of side effects and possessing extremely high safety; and transgenic mammals. The present invention also provides processes for efficient manufacturing of the functional molecules; and processes for treating gastric cancer or gastric ulcers and preventing gastric ulcers which include administering the functional molecules thereby being free of side effects and possessing extremely high safety.

Figure 1:
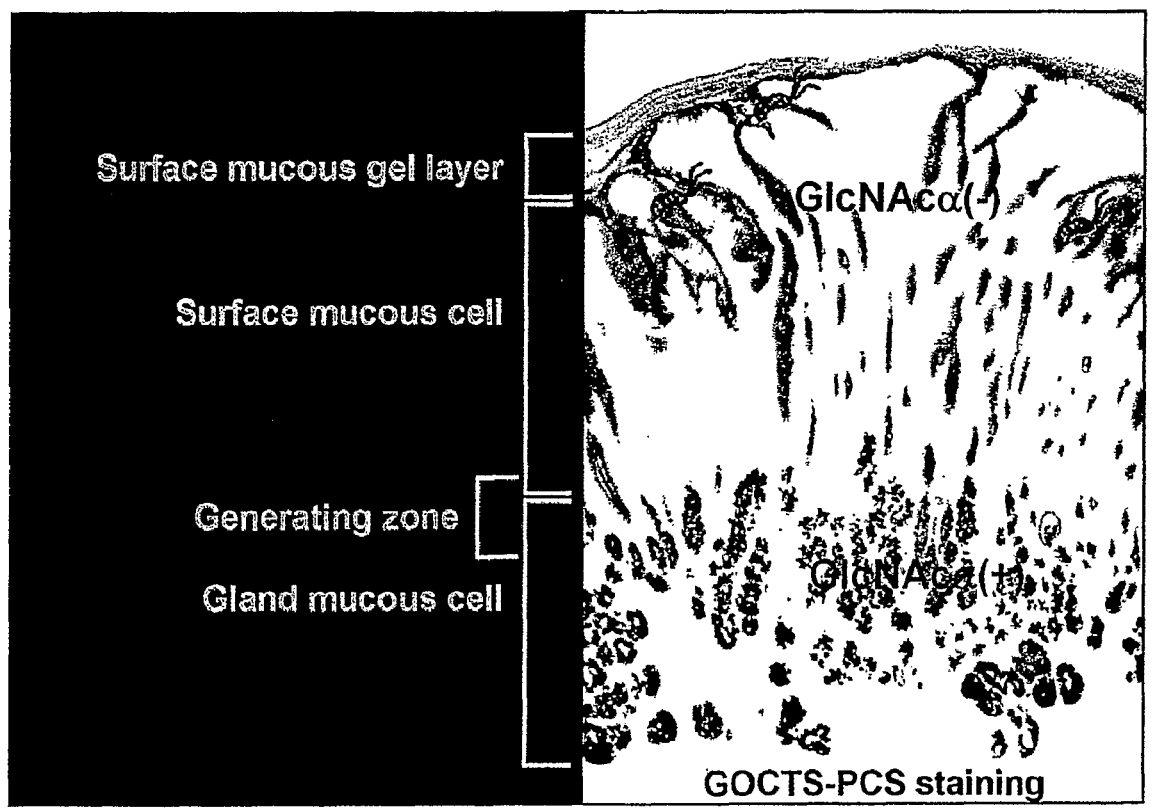
FIG. 1 provides a schematic cross-sectional view of a general gastric wall of humans, showing that α1,4-GlcNAc residues are stained by PCS staining, whereas GOCTS stains superficial mucins.

As shown in FIG. 1, when patients infected with *Helicobacter pylori* are examined, the microbes are solely associated with surface mucous cell-type mucin secreted from surface mucous cells, which constitute the surface portion of stomach lining, but do not colonize the gland mucous cells, which are present in the deeper portions of the stomach lining. It is also found that gland mucous cell-type mucin, secreted from gland mucous cells, contains N-acetylglucosamine residues which are linked at its terminals by the α1,4-glycosidic bonds (herein after may be referred to as a "GlcNAcα" residue), and that the terminal GlcNAc α residues inhibit the synthesis of cholesteryl-α-D-glucopyranoside (CGL), which is contained in the cell wall of *H. pylori*, resulting possibly in inhibiting the growth properties of *H. pylori*, additionally inhibiting the motility thereof, and causing abnormal morphologies thereof. In FIG. 1, "GlcNAcα (+)" means that mucin containing a GlcNAcα residue is present, and "GlcNAcα (−)" means that mucin with no GlcNAcα residue is present. It is derived from the fact that α1,4-GlcNAc residues can be stained by PCS, whereas GOCTS stains superficial mucins (see, also, Example 1).

The present invention provides a molecule, comprising a plurality of monomer units, wherein at least one of the monomer units is an N-acetylglucosamine residue. As disclosed herein, a molecule of the invention suppresses or inhibits the synthesis of cholesteryl-α-D-glucopyranoside and, in turn, suppresses and inhibits the growth of bacteria requiring the cholesteryl-α-D-glucopyranoside. Moreover, the molecule suppresses or inhibits the motility of bacteria requiring the cholesteryl-α-D-glucopyranoside, and causes abnormal morphologies of the bacteria. In one embodiment, the molecule comprises a sugar chain, which can contain an N-acetylglucosamine residue at a terminal of the molecule. In one aspect, the N-acetylglucosamine residue is an α1,4-N-acetylglucosamine residue. The α1,4-N-acetylglucosamine residue can suppress and inhibit the synthesis of cholesteryl-α-D-glucopyranoside and, in turn, suppress and inhibit the growth of bacteria requiring the cholesteryl-α-D-glucopyranoside. Moreover, it suppresses or inhibits the motility of bacteria requiring the cholesteryl-α-D-glucopyranoside, and causes abnormal morphologies of the bacteria. A molecule of the invention can further include a galactose residue, wherein the galactose residue is adjacent to the N-acetylglucosamine residue. The molecule can be linear or branched.

A molecule of the present invention contains, as a portion thereof, an N-acetylglucosamine ("GlcNAc") and optionally contains a molecule constituting unit selected properly as needed. The GlcNAc residue can be a chemically synthesized product, an extract from natural products, or that existing in the living body. GlcNAc can be produced by any process, including, for example, by hydrolyzing chitin in hydrochloric acid and then isolating the hydrolysate.

Units comprising the molecule can be selected for specific purposes as disclosed herein, and include, for example, sugar residues and resin units, which can be used alone or in combinations of two or more. The sugar residues can be monosaccharide residues or polysaccharide residues. Examples of the monosaccharide residues or monosaccharide residues constituting polysaccharide residues include galactose, tetrose, erythrose, threose, pentose, ribose, arabinose, xylose, lyxose, hexose, arose, altrose, glucose, mannose, gulose, idose, talose, tetrulose, erythrulose, ribulose, xylulose, psicose, fructose, sorbose, tagatose, 2-hepturose, sedoheptulose, quinovose, rhamnose, fucose, digitoxose, abequose, tyvelose, 2-deoxyribose, 2-deoxyglucose, glucosamine, mannosamine, galactosamine, fucosamine, quinovosamine, rhamnosamine, neuraminic acid, muramic acid, and nojirimycin residues. Of these, galactose residue is especially preferred as a sugar residue adjacent to the GlcNAc residue. Such sugar residues can be used alone or in combinations of two or more, and can further contain a substituent inserted therein or can be substituted with another substituent. Examples of the resin unit include L-lactide and D-lactide. Such units as exemplified herein and otherwise known in the art preferably are biocompatible molecules.

A GlcNAc residue can be in any position in a molecule of the invention, including, for example, at a terminal position of the molecule or at a position other than a terminal position. Positioning of a GlcNAc residue at the terminal position, however, can provide excellent antibacterial effects. When the molecule comprises a sugar chain, linkage of the GlcNAc residue can be via any means, including, for example, an α-glycoside linkage or a β-glycoside linkage. In one aspect, the linkage is an α1,4-glycoside linkage.

Where an enzyme is used to link the GlcNAc residue to the molecule through the α1,4-glycoside linkage and it can be selected as needed, depending on the purpose. For example, the linking enzyme can be N-acetylglucosaminyl transferase (α4GnT; see JP-A No. 2001-46077). α4GnT can be produced, for example, by forming a DNA encoding the α4GnT in accordance with the process as described in JP-A No. 2001-46077, transfecting various cells with a vector having the DNA incorporated therein and causing expression of the α4GnT (see, also, Nakayama et al., Proc. Natl. Acad. Sci. U.S.A. 96, 8991, 1999).

The molecule can contain any number of monomer units, including GlcNAcα residues and additional units, as desired, and can be selected as needed depending on the using purpose. For example, the molecule can contain 2 or more monomer units, particularly 2 to 30 monomer units (e.g., 5 to 20 monomer units). Generally, when the number of monomer units is less than 2, the molecule lacks a significant antibacterial effect.

A molecule of the invention can be linear or branched. When branched, the number of branches is not particularly limited and may be selected as needed depending on the using purpose. In general, the greater the number of branches, the greater the antibacterial effect. Any enzyme can be used for branching the molecule, including, for example, core 2β1,6-N-acetylglucosaminyl transferase-I (C2GnT-I), which can be produced, for example, by introducing a gene into a cell, preparing C2GnT-I by genetic modification, isolating and purifying from an organism, or the like (see, e.g., Bierhuizen and Fukuda, Proc. Natl. Acad. Sci. U.S.A. 89, 9326, 1992). Similarly, any enzyme can be used for binding a sugar residue in the molecule, including, for example, core 1 elongation β1,3-N-acetylglucosaminyl transferase (C1-β3GnT) can be used (see, e.g., Yeh et al., Cell 105:957-969, 2001).

When the molecule of the present invention comprises a sugar chain containing a GlcNAcα residue, it can be similar to a molecule possessed by gland mucous cell-type mucin secreted from gland mucous cells existing in the deep portion of the human stomach wall, or a molecule having a structure analogous thereto. As such, the molecule is not expected to have any side effects, and is highly safe even when used as a pharmaceutical or an edible composition such as food or beverage.

The invention also provides a composition, which contains a molecule, comprising a plurality of monomer units, wherein at least one of the monomer units is an N-acetylglucosamine residue. The composition can be useful, for example, as a pharmaceutical (e.g., a medicament) and/or can be an edible composition such as food and/or beverage.

Further provided is a functional molecule, comprising a molecule, comprising a plurality of monomer units, wherein at least one of the monomer units is an N-acetylglucosamine residue. The functional molecule can suppress and/or inhibit the synthesis of cholesteryl-α-D-glucopyranoside and, in turn, can suppress and/or inhibit the growth of bacteria requiring the cholesteryl-α-D-glucopyranoside. In one aspect, the functional molecule suppresses or inhibits the motility of bacteria requiring the cholesteryl-α-D-glucopyranoside, and causes abnormal morphologies of the bacteria. Such a functional molecule can contain a main chain and a side chain, wherein the side chain can be a molecule, comprising a plurality of monomer units, wherein at least one of the monomer units is an N-acetylglucosamine residue.

A functional molecule of the invention comprises the above-described molecule of the present invention and optionally comprising at least one other molecule. Generally, the functional molecule has a main chain and a side chain, and, particularly, wherein a molecule of the invention comprises the side chain. The molecule can exist in a cluster form relative to the main chain. The term "in the cluster form" as used herein means a state in which 10 or more molecules, as disclosed herein, are linked, at the terminals thereof, to one main chain. There is no limitation imposed on a ratio of the number of the main chain to the number of the side chains and it can be selected as needed, depending on the using purpose. For example, when the main chain is a protein, the ratio is limited by the types of the amino acid residues which constitute the protein. In general, the greater the number of side chains relative to one main chains, the greater the antibacterial effect of the functional molecule.

An "other molecule", which can be linked to a molecule of the invention, can be selected as needed, depending on the using purpose, and including, for example, sugar chains, polypeptides, lipids, glycolipids, sugar proteins, nucleotides, and resins such as polylactic acid, which can be used alone or in combinations of two or more. In one example, the other molecule comprises a polypeptides, including, for example, CD43, CD34 and/or Muc-6. No particular limitation is imposed on the amino acid, in the polypeptide that will bind to (link) the molecule. Examples include phenylalanine (Phe), leucine (Leu), isoleucine (Ile), methionine (Met), valine (Val), serine (Ser), proline (Pro), threonine (Thr), alanine (Ala), tyrosine (Tyr), histidine (His), glutamine (Gln), asparagine (Asn), lysine (Lys), aspartic acid (Asp), glutamic acid (Glu), cysteine (Cys), tryptophan (Trp), arginine (Arg) and glycine (Gly). Generally, serine and/or threonine is used.

As disclosed herein, a functional molecule of the invention can suppress and/or inhibit the synthesis of the CGL. By suppressing or inhibiting the synthesis of the CGL, growth of bacteria requiring the CGL can be suppressed or inhibited. Examples of the bacteria requiring the CGL include *Helicobacter* genus bacteria, which includes *Helicobacter pylori*. The *Helicobacter* genus bacteria contain, in the cell walls thereof, α-cholesteryl glucoside ("α-CGs"). Examples of the main components of the α-CGs include CGL, cholesteryl-6-O-tetradecanoyl-α-D-glucopyranoside ("CAG") and cholesteryl-6-O-phosphatidyl-α-D-glucopyranoside ("CPG"). *Helicobacter* genus bacteria are one type of bacteria needing, for their survival, synthesis of CGL.

In humans, the functional molecule of the present invention possesses antibacterial activity selectively and specifically against *Helicobacter* genus bacteria, and does not damage the bacterial layer in the intestine. Additionally, when the functional molecule includes a GlcNAcα residue, it is identical with gland mucous cell-type mucin secreted from gland mucous cells present in the deeper portion of human gastric wall or other functional molecules having structures similar to that of the mucin. Hence, the functional molecule can be used as pharmaceutical, food, or beverage without side effects, which makes it extremely safe and therefore advantageous.

The main chain of such a functional molecule can be, for example, a polypeptide, and in one aspect, the molecule comprising a plurality of monomer units, wherein at least one of the monomer units is an N-acetylglucosamine residue, exists in the cluster form relative to the main chain. Such a functional molecule, wherein the molecule comprising a plurality of monomer units, wherein at least one of the monomer units is an N-acetylglucosamine residue, that exists in the cluster form relative to the main chain, can suppress and inhibit the synthesis of cholesteryl-α-D-glucopyranoside and in turn, suppresses and inhibits the growth of bacteria requiring the cholesteryl-α-D-glucopyranoside. Moreover, it suppresses or inhibits the motility of bacteria requiring the cholesteryl-α-D-glucopyranoside, and causes abnormal morphologies of the bacteria.

As such, a functional molecule of the invention can suppress and/or inhibit the synthesis of cholesteryl-α-D-,glucopyranoside (CGL), can suppress and/or inhibit the synthesis of cholesteryl-α-D-glucopyranoside, and/or can suppress and/or inhibit the growth of bacteria requiring the cholesteryl-α-D-glucopyranoside. Moreover, it can suppress and/or inhibit the motility of bacteria requiring the cholesteryl-α-D-glucopyranoside, and cause abnormal morphologies of the bacteria. A functional molecule of the invention is exemplified by a molecule in which the polypeptide is CD43, CD34, or Muc-6. In one aspect, the ratio of the number of side chains to the main chain is 10 or more.

A functional molecule of the invention can be used, for example, to treat, ameliorate, and/or remedy a gastric ulcer, a duodenal ulcer, an anti-*H. pylori* agent, gastritis, and/or chronic gastritis. The functional molecule also can be used for an edible composition such as food or beverage. Accordingly, a composition containing such a functional molecule is provided, wherein the composition can suppress and/or inhibit the synthesis of cholesteryl-α-D-glucopyranoside; can suppress and/or inhibit the growth of bacteria requiring the cholesteryl-α-D-glucopyranoside; can suppress and/or inhibit the motility of bacteria requiring the cholesteryl-α-D-glucopyranoside; and/or can cause abnormal morphologies of the bacteria. Also provided is a pharmaceutical containing a functional molecule of the invention having such suppressing and/or inhibiting activities. Such a pharmaceutical composition can be provided in various forms and, as such, can, for example, be sprayed on or coated to the mucous layer of the stomach and/or intestine of a subject to be treated. In various aspects, the pharmaceutical composition can be used after being impregnated or incorporated into a film and/or sheet, which can be applied to the mucous layer of the stomach and/or intestine. A pharmaceutical composition of the invention can contain at least one of a cholesterol degradative enzyme, which degrades cholesterol, and a glucose degradative enzyme, which degrades glucose. As such, the pharmaceutical composition can have the suppressing and/or inhibiting activities as disclosed herein.

The invention further provides an edible composition, which comprises a functional molecule, which comprises a molecule comprising a plurality of monomer units, wherein at least one of the monomer units is an N-acetylglucosamine residue. Such an edible composition similarly can suppress and/or inhibit the synthesis of cholesteryl-α-D-glucopyranoside; can suppress and/or inhibit the growth of bacteria requiring the cholesteryl-α-D-glucopyranoside; can suppress and/or inhibit the motility of bacteria existing in a living organism and requiring the cholesteryl-α-D-glucopyranoside; and can cause abnormal morphologies of the bacteria.

The present invention also relates to a process for producing a functional molecule having at least one α1,4-N-acetylglucosamine residue. Such a process can be performed, for example, by contacting α4GnT, at least one of C2GnT-I and C1-β3GnT, and a polypeptide having at least one O-glycosylated region, thereby producing a functional molecule having at least one α1,4-N-acetylglucosamine residue. According to one embodiment of the present process, the α4GnT, at least one of C2GnT-I and C1-β3GnT, and the polypeptide having at least one O-glycosylated region are contacted, thereby producing the functional molecule. In one aspect of this embodiment, the polypeptide is a soluble polypeptide (e.g., CD43, CD34, or Muc-6). In another aspect, the polypeptide is mucin secreted into milk of mammals.

A process for producing a functional molecule according to the present invention can further include isolating the functional molecule having at least one α1,4-N-acetylglucosamine residue after production thereof. Accordingly, the invention provides a functional molecule obtained by the present process, wherein the isolated functional molecule has suppressing and/or inhibiting activity as disclosed herein. For example, by administering the isolated functional molecule (e.g., as a pharmaceutical), it can suppress and/or inhibit the motility of bacteria existing in a living organism and requiring the cholesteryl-α-D-glucopyranoside, and can cause abnormal morphologies of the bacteria.

The invention further relates to a process for producing a recombinant functional molecule having at least one α1,4-N-acetylglucosamine residue. Such a process can be performed, for example, by expressing, in a eukaryotic cell, a first polynucleotide encoding α4GnT, a second polynucleotide encoding at least one of C2GnT-I and C1-β3GnT, and a third polynucleotide encoding a polypeptide having at least one O-glycosylated region. According to such a process, at least one of the first, second and/or third polynucleotides is an exogenous polynucleotide introduced into the eukaryotic cell. For example, the process can be performed by expressing, an α4GnT, at least one of C2GnT-I and C1-β3GnT, and a polypeptide having at least one O-glycosylated region are expressed. Subsequently, the α4GnT, at least one of C2GnT-I and C1-β3GnT, and polypeptide having at least one O-glycosylated region can be with each other, thereby producing a functional molecule. As disclosed herein, the polypeptide can be a soluble polypeptide (e.g., CD43, CD34, and Muc-6). The eukaryotic cell in which the recombinant functional molecule is made can be, for example, a cell of a mammal.

According to the present invention, the process for producing a recombinant functional molecule can further include contacting the α4GnT-I, at least one of the C2GnT-I and the C1-β3GnT, and the polypeptide having at least one O-glycosylated region, after expressing, thereby producing a recombinant functional molecule having at least one α1,4-N-acetylglucosamine residue. Such a process can further include isolating the recombinant functional molecule having at least one α1,4-N-acetylglucosamine residue after production thereof. As such, an isolated recombinant functional molecule produced according to such a process also is provided, said isolated recombinant functional molecule having suppressing and/or inhibiting activity as disclosed herein.

The present invention also provides a non-human transgenic mammal that is capable of secreting milk. Such a non-human transgenic mammal of the invention can contain, in its genome, a first polynucleotide encoding α4GnT; a second polynucleotide encoding at least one of C2GnT-I and C1-β3GnT; and a third polynucleotide encoding a polypeptide having at least one O-glycosylated region. In such a transgenic mammal, an α4GnT, at least one of C2GnT-I and C1-β3GnT, and a polypeptide having at least one O-glycosylated region can be expressed. Subsequently, the α4GnT, at least one of C2GnT-I and C1-β3GnT, and polypeptide having at least one O-glycosylated region can contact each other, thereby producing a functional molecule.

A transgenic non-human mammal of the invention can contain an exogenous first polynucleotide, second polynucleotide and/or third polynucleotide. In one aspect, at least one of the first polynucleotide, second polynucleotide and third polynucleotide is introduced into the genome so as to be linked operatively with at least one of the 5' regulatory sequence and 3' regulatory sequence of a gene relating to the mammary gland of a mammal. In another aspect, the third polynucleotide is introduced into the genome so as to be operatively linked with a nucleotide sequence encoding a signal sequence having effects of causing the polypeptide having at least one O-glycosylated region to be secreted in the milk. A 5' regulatory sequence, to which a polynucleotide is operatively linked, can comprise a promoter, including, for example, a whey acidic protein (WAP) promoter, an α-casein promoter, a β-casein promoter, a γ-casein promoter, and α-lactalbumin promoter or a β-lactoglobulin promoter. In still another aspect, the first, second and third polynucleotides form one nucleic acid molecule, which is introduced into the genome of the transgenic non-human mammal so as to be operatively linked with either one of the 5' regulatory sequence and 3' regulatory sequence of a gene relating the mammary gland. The transgenic mammal can be any mammal capable of producing milk, including, for example, a mouse, rat, rabbit, horse, pig, sheep, goat, or cow.

Whether the transgenic mammal requires the second exogenous polynucleotide can be determined by noting whether cells produce the functional molecule of the invention express the endogenous C2GnT-I under natural conditions, in which case introduction of the second exogenous polynucleotide is not necessary. Whether one needs to introduce into the transgenic mammal the third exogenous polynucleotide or not is determined by noting whether cells producing the functional molecule of the present invention express the endogenous polypeptide having at least one O-glycosylated region under natural conditions, in which case introduction of the third exogenous polynucleotide is not necessary. For example, when the cells are mammary epithelial cells, the mammary epithelial cells express the C2GnT-I and the polypeptide having at least one o-glycosylated region so that a transgenic mammal having the mammal epithelial cells do not necessarily need the second and third polynucleotides to be introduced therein.

In the transgenic mammals of the present invention, the polypeptide having at least one O-glycosylated region is glycosylated by the α4GnT and at least either one of the C2GnT-I and C1-β3Gn so that when they are females capable of secreting the milk, they can secret the functional molecule of the present invention in their milk. The production process of a transgenic mammal which is other than humans and can secret a recombinant type polypeptide in its milk is known. The transgenic mammal can be produced by such a known method (see, e.g., U.S. Pat. Nos. 6,344,596; 6,548,735; 6,222,094; 5,962,648; 5,891,698; and 5,850,000)

The present invention also relates to a process for producing a recombinant functional molecule having at least one α1,4-N-acetylglucosamine residue. Such a method can be performed, for example, by introducing a first polynucleotide encoding α4GnT into an embryo of a mammal other than humans; transplanting the embryo to a recipient female mammal; causing the recipient female mammal to produce offspring thereof; and causing female offspring, among offspring produced, to produce milk. According to the present process, an α4GnT is expressed in the body of the offspring. In one aspect, the α4GnT at least contacts with a polypeptide which is present in the body of the offspring thereby producing a functional molecule. According to another aspect of the present process, the first polynucleotide is introduced into the embryo so as to be operatively linked with at least one of the 5' regulatory sequence and 3' regulatory sequence of a gene relating to the mammary gland of a mammal. In one embodiment of the process for producing a recombinant functional molecule, the process includes introducing into the embryo a second polynucleotide encoding at least one of C2GnT-I and C1-β3GnT, and a third polynucleotide encoding a polypeptide having at least one O-glycosylated region. In another embodiment, the process further includes milking after causing the female offspring to produce milk, and in one aspect can further include isolating the recombinant functional molecule from the milk. Accordingly, the invention also provides milk obtained by such a process, wherein the milk, particularly the recombinant functional molecule therein, has suppressing and/or inhibiting activity as disclosed herein.

A functional molecule of the present invention can be produced by any one of the methods as disclosed herein, or can be produced in any other way that will be known or routine based on the present disclosure. Three aspects of the production processes of the functional molecule are exemplified herein, and the milk of the present invention will be revealed through the description of the functional molecule of the present invention. The first aspect of the production process is a production process of a functional molecule having at least one α1,4-N-acetylglucosamine residue, which comprises bringing α4GnT, at least one of C2GnT-I and C1-β3GnT, and a polypeptide having at least one O-glycosylated region into contact with each other. The second aspect of the production process is a production process of a recombinant type functional molecule having at least one α1,4-N-acetylglucosamine residue, which comprises at least a step of expressing, in eukaryotic cells, a first polynucleotide encoding α4GnT, a second polynucleotide encoding at least one of C2GnT-I and C1-β3GnT, and a third polynucleotide encoding a polypeptide having at least one O-glycosylated region. The third aspect of the production process is a production process of a recombinant type functional molecule having at least one α1,4-N-acetylglucosamine residue, which comprises introducing a first polynucleotide encoding α4GnT into an embryo of a mammal other than humans, transplanting the resulting embryo to a recipient female mammal, causing the female mammal to produce offspring thereof, and causing a female offspring, among offspring produced, to produce milk. The α4GnT, the C2GnT-I and the C1-β3GnT are as described above. The polypeptide can be any polypeptide that comprises at least one O-glycosylated region (e.g., CD43, CD34, Muc-6, and mucin) and can be secreted in the milk of mammals.

In the above-described first aspect, the GlcNAc and sugar, in addition to the α4GnT, at least either one of the C2GnT-I and the C1-β3GnT and the polypeptide having at least one O-glycosylated region, can be contacted with each other. In the above-described second aspect, the functional molecule can be produced by contacting the α4GnT, at least either one of the C2GnT-I and the C1-β3GnT and the polypeptide having at least one O-glycosylated region with each other after the expression step, then further contacting with the GlcNAc and sugar. Also, in the second aspect of the production process, each of the first to third polypeptides can be exogenous or endogenous. The term "endogenous" as used herein means that when it is used concerning polynucleotide, the polynucleotide is found in specific cells or cells of organisms under natural conditions, while the term "exogenous" means that when it is used concerning polynucleotide, the polynucleotide is not found in specific cells or cells of organisms under natural conditions.

Any eukaryotic cells can be used in the present methods. Generally, the cells are mammalian cells, including, for example, ovarian cells (e.g., CHO cells) and mammary cells. When the eukaryotic cells are mammary gland cells, the functional molecule can be produced by supplying the α4GnT as an exogenous one, because they can express C2GnT-I and the polypeptide having at least one O-glycosylated region. When the eukaryotic cells express the C2GnT-I, the functional molecule can be produced by supplying the α4GnT and the polypeptide having at least one O-glycosylated region as exogenous ones.

An example of the second aspect of the production process as described above can include amplifying a DNA fragment (e.g., a portion encoding the amino acids 20 to 254 of SEQ ID NO: 1), including the whole extracellular domain of the CD43 by PCR, and subcloning the amplified DNA fragment into a vector such as pSecTag2 (Invitrogen Corp.) such that an Igκ leader peptide, myc epitope follow it and a vector (pSecTag2-sCD43) encoding (His)$_6$ is produced. Then, four vectors having, incorporated in the pSecTag2-sCD43, (1) a polynucleotide (cDNA) encoding C2GnT-I, (2) a polynucleotide (cDNA) encoding α4GnT, (3) a polynucleotide (cDNA) encoding soluble CD43, and (4) a polynucleotide (cDNA) encoding a polyoma.virus large T antigen, respectively are transfected into the CHO.Lec2 cells, which have been cultured in advance, by using LipofectAmine™ reagent (Invitrogen Corp.) to cause expression of the C2GnT-I, α4GnT, soluble CD43 and polyoma.virus large T antigen in the resulting CHO.Lec2 cells and contacting them with each other, whereby the soluble CD43 containing a terminal GlcNAcα residue can be expressed as the functional molecule.

In the third aspect of the production process, the first polynucleotide and, if needed, at least one of the second polynucleotide and the third polynucleotide are introduced into the embryo of a mammal other than humans. The first polynucleotide can be introduced into an embryo in a way that it can mutually act with at least one of 5' regulatory sequence and 3' regulatory sequence of a gene relating to the mammary gland of a mammal. In such case, one or both of the second and third polynucleotides can be introduced into the embryo in a way that they can mutually act with at least one of the 5' regulatory sequence and 3' regulatory sequence of a gene relating to the mammary gland of a mammal. No particular limitation is imposed on the gene relating to the mammary gland, although it generally is a mammary gland specific gene. The 5' regulatory sequence can be any regulatory element as desired, and generally includes a promoter, as disclosed herein.

When the third polynucleotide encoding the polypeptide having at least one O-glycosylated region is introduced into a control element (for example, mammary gland specific promoter) in at least one of the 5' regulatory sequence and 3' regulatory sequence so that they are operatively linked, the control element controls the polynucleotide in a manner similar to that employed for another polynucleotide sequence related within the ordinary cells and the encoded polypeptide can be expressed tissue-specifically within mammary epithelial cells. It is also possible to introduce the first polynucleotide sequence in the second polynucleotide sequence so that they are operatively linked and to cause expression of two or more polypeptides from the polynucleotide thus introduced to be operatively linked. If necessary, a chimeric (combined) polypeptide can be expressed from the polynucleotide thus introduced to be operatively linked. The chimeric polypeptide may be a fused polypeptide. The fused polypeptide is a single polypeptide obtained by the translation of the above-described two or more encoded polypeptides, that is, a polypeptide obtained by covalent bonding of these polypeptides by a peptide bond.

The third polynucleotide can be introduced into an embryo to be operatively linked with a nucleotide sequence encoding a signal sequence having effects of causing a polypeptide having at least one O-glycosylated region to be secreted in milk. The milk may be obtained after causing the female offspring to produce it and the functional molecule may be isolated from the milk. In the third aspect of the production process, the α4GnT expresses from the first polynucleotide in the body of the female offspring, and the endogenous or exogenous polypeptide having at least one O-glycosylated region is glycosylated by at least either one of the C2GnT-I or C1-β3GnT, whereby the functional molecule can be produced. The functional molecule is contained in the milk of the female offspring so that it can be produced efficiently by milking.

As disclosed herein, a functional molecule of the invention can be used in various fields. It can be suitably used for remedies for diseases caused by *H. pylori*, including, for example, as a remedy for gastric ulcer, for duodenal ulcer, for gastritis, or for alleviating chronic gastritis, particularly when provided as composition, pharmaceutical, and/or food or beverage. A composition, pharmaceutical, and food or beverage of the present invention contains at least either one of the molecules and the functional molecule of the present invention and in addition, optionally contains another component selected as needed. No particular limitation is imposed on the content of the at least one of the molecules and functional molecule in the total amount of the composition, pharmaceutical, or food or drink of the present invention and it can be selected as needed, depending on the using purpose. The content (amount) of the molecule in the total amount of the molecule, functional molecule, pharmaceutical, or composition of the present invention can be selected as needed and, generally, the higher the content, the greater the antibacterial effect.

The compositions, in various forms, can contain other components, which can be selected as needed, depending on the using purpose. Examples of such other components include excipients, lubricants, binders, water soluble polymers, basic inorganic salts, solvents, solubilizing agents, suspending agents, isotonizing agents, buffering agents, soothing agents, antiseptics, antioxidants, coloring agents, sweeteners, acidulants, effervescents, and perfumes. For efficiently suppressing or inhibiting the synthesis of CGL, addition of a cholesterol degradative enzyme or glucose degradative enzyme can be useful. Examples of excipients include lactose, sucrose, D-mannitol, starch, corn starch, crystalline cellulose, light silicic anhydride and titanium oxide. Examples of lubricants include magnesium stearate, sucrose fatty acid ester, polyethylene glycol, talc, and stearic acid. Examples of binders include hydroxypropyl cellulose, hydroxypropyl methylcellulose, crystalline cellulose, starch, polyvinylpyrrolidone, gum arabic powder, gelatin, pullulan, and low-substituted hydroxypropyl cellulose. Examples of water soluble polymers include cellulose derivatives such as hydroxypropyl cellulose, hydroxypropyl methylcellulose, methylcellulose and carboxymethylcellulose sodium, polyvinylpyrrolidone, sodium polyacrylate, polyvinyl alcohol, sodium alginate and guar gum. Examples of basic inorganic salts include basic inorganic salts with sodium, potassium, magnesium or calcium. Examples of the basic inorganic salt with sodium include sodium carbonate, sodium hydrogencarbonate and disodium hydrogenphosphate. Examples of basic inorganic salts with potassium include potassium carbonate, and potassium hydrogencarbonate. Examples of basic inorganic salts with magnesium include heavy magnesium carbonate, magnesium carbonate, magnesium oxide, magnesium hydroxide, magnesium aluminometasilicate, magnesium silicate, magnesium aluminate, synthetic hydrotalcite ($Mg_6Al_2(OH)_{16}.CO_3.4H_2O$) and alumina oxide.magnesium. Examples of basic inorganic salts with calcium include precipitated calcium carbonate and calcium hydroxide. Examples of solvents include distilled water for injection, alcohol, propylene glycol, macrogol, sesame oil, corn oil and olive oil. Examples of solubilizing agents include polyethylene glycol, propylene glycol, D-mannitol, benzyl benzoate, ethanol, tris-aminomethane, cholesterol, triethanolamine, sodium carbonate, and sodium citrate. Examples of suspending-agents include surfactants such as stearyltriethanolamine, sodium lauryl sulfate, laurylaminopropionic acid, lecithin, benzalkonium chloride, benzethonium chloride and glycerin monostearate; and hydrophilic polymers such as polyvinyl alcohol, polyvinylpyrrolidone, carboxymethylcellulose sodium, methylcellulose, hydroxymethylcellulose, hydroxyethylcellulose and hydroxypropylcellulose. Examples of isotonizing agents include glucose, D-sorbitol, sodium chloride, glycerin and D-mannitol. Examples of buffering agents include phosphates, acetates, carbonates and citrates. Examples of soothing agents include benzyl alcohol. Examples of antiseptics include paraoxybenzoates, chlorobutanol, benzyl alcohol, phenethyl alcohol, dehydroacetic acid and sorbic acid. Examples of antioxidants include sulfites, ascorbic acid and α-tocopherol. Examples of coloring agents include food dyes such as Food Yellow No. 5, Food Red No. 2 and Food Blue No. 2, food lake dyes and red iron oxide. Examples of sweeteners include saccharin sodium, dipotassium glycyrrhizinate, aspartame, stevia and thaumatin. Examples of acidulants include citric acid (citric anhydride), tartaric acid and malic acid. Examples of effervescents include sodium bicarbonate. Examples of perfumes include extracts from lemon, lime, orange, menthol and strawberry.

The compositions and/or pharmaceuticals of the present invention can be administered in any form or any manner as is useful for the purpose of the administration. As such, administration may be oral, or the composition (or functional molecule)can be directly sprayed or coated onto the mucous layer of at least one of the human stomach or intestine. The composition or pharmaceutical of the present invention also can be used following impregnation in a film or sheet, which can be applied to the stomach and/or intestine. Such administration is advantageous, because the composition or pharmaceutical sprayed or coated to the film or sheet can be maintained for a predetermined time without dropping therefrom over the surface of the mucous layer of the stomach or intestine, making it possible to administer the intended amount of the composition or pharmaceutical and have sufficient antibacterial effects. For the above-described using method, known medical instruments such as endoscope are preferably used. When the affected area includes the stomach, the film or sheet preferably contains chitin, sugar and a fat component. When the affected area is intestine, chitin is preferred. Incorporation of such a substance makes it possible to bring the functional molecule into contact with the affected area for long hours without causing decomposition of the molecule by the gastric or intestinal juice in the stomach or intestine.

A composition, pharmaceutical and food or beverage according to the present invention has sufficient antibacterial effects. In order to improve the effects further, at least one of known antibiotics and crude drugs which are remedies for gastric ulcer, remedies for duodenal ulcer, anti-*Helicobacter pylori* agents, remedies for gastritis, or drugs for alleviating chronic gastritis may be used in combination. Since the composition, pharmaceutical and food or beverage according to the present invention contains the functional molecule (or the molecule) of the present invention, it is of great advantage with high safety and without side effects and, therefore, can be used in various fields. For example, it can suitably be used for remedies for diseases caused by *H. pylori* (e.g., remedies for gastric ulcer, remedies for duodenal ulcer, anti-*H. pylori* agents, remedies for gastritis, and drugs for alleviating chronic gastritis), particularly for the pharmaceutical and food or beverage of the present invention. The food or beverage of the present invention can be used suitably for soft drinks, carbonated drinks, energy drinks, fruit juices, lactic acid beverages, dietary supplements, frozen deserts, noodles, confectionery, marine products, milk products, processed foods, seasonings, tablets and capsules.

Accordingly, the present invention relates to a process for inhibiting bacterial growth. Such a process can be practiced, for example, by contacting bacteria expressing CGL with a functional molecule having at least one α1,4-N-acetylglucosamine residue so as to suppress or inhibit at least one of growth of the bacteria and formation of cell walls of the bacteria. According to this process, the functional molecule suppresses and inhibits the expression (synthesis) of cholesteryl-α-D-glucopyranoside and, in turn, suppresses and inhibits at least one of the growth of bacteria requiring the cholesteryl-α-D-glucopyranoside and formation of cell walls of the bacteria. Moreover, it suppresses or inhibits the motility of bacteria requiring the cholesteryl-α-D-glucopyranoside, and causes abnormal morphologies of the bacteria. The functional molecule can having an α1,4-N-acetylglucosamine residue can suppress or inhibit the activity of UDP-Glc:sterol glycosyltransferase. Bacteria, for which growth is suppressed and/or inhibited, can be, for example, a *Helicobacter* genus bacteria (e.g., *H. pylori*).

The invention further provides a process for treating gastric ulcer. Such a method can be practiced, for example, by administering a functional molecule having an α1,4-N-acetylglucosamine residue so as to alleviate signs or symptoms of gastric ulcer induced by the infection of a subject with *Helicobacter* genus bacteria. In the process for treating gastric ulcer, the functional molecule suppresses and inhibits the expression (synthesis) of cholesteryl-α-D-glucopyranoside and, in turn, alleviates signs or symptoms of gastric ulcer induced by the infection with the *Helicobacter* genus bacteria, which requires cholesteryl-α-D-glucopyranoside. The *Helicobacter* genus bacteria can be *H. pylori*, and the subject can be a mammal, including, for example, a mouse, rat, rabbit, horse, pig, sheep, goat or cow, and particularly a human subject.

A process for treating gastric ulcer can utilize a functional molecule having an α1,4-N-acetylglucosamine residue comprising a gland mucous cell-type mucin. The functional molecule can be administered in any of various ways, including, for example, orally, by spraying and/or coating the gastric mucous layer, or by applying a film and/or a sheet containing the functional molecule. In one aspect, the functional molecule is administered by using milk produced as disclosed herein.

The present invention further relates to a process for preventing gastric ulcer. Such a method can be performed, for example, by administering a functional molecule having an α1,4-N-acetylglucosamine residue so as to prevent signs or symptoms of gastric ulcer induced by the infection of a subject with *Helicobacter* genus bacteria, wherein the functional molecule suppresses and/or inhibits the expression (synthesis) of cholesteryl-α-D-glucopyranoside, and prevents signs or symptoms of gastric ulcer induced by the infection with the *Helicobacter* genus bacteria, which requires cholesteryl-α-D-glucopyranoside. The functional molecule having an α1,4-N-acetylglucosamine residue can comprise a gland mucous cell-type mucin, and can be administered as disclosed herein or otherwise known in the art.

In addition, the invention relates to a process for treating gastric cancer. Such a method can be performed, for example, by administering a functional molecule having an α1,4-N-acetylglucosamine residue to alleviate signs or symptoms of gastric cancer induced by the infection of a subject with *Helicobacter* genus bacteria, wherein the functional molecule suppresses and inhibits the expression (synthesis) of cholesteryl-α-D-glucopyranoside and, in turn, alleviates signs or symptoms of gastric cancer induced by the infection with the *Helicobacter* genus bacteria.

The invention provides a non-naturally occurring compound, which includes at least one terminal α1,4-linked N-acetylglucosamine (α1,4-linked GlcNAc) residue operatively linked to a carrier molecule. The term "operatively linked" is used broadly herein to refer to two or more molecules that are positioned with respect to each other such that they act as a single unit and effect a function attributable to one or both molecules or a combination thereof. For example, reference to an a α1,4-linked GlcNAc residue operatively linked to a carrier molecule means that the α1,4-linked GlcNAc residue is positioned such that it has the effect of reducing or inhibiting growth of a *Helicobacter* species such as *H. pylori*. Such an operatively linked α1,4-linked GlcNAc residue is exemplified herein by CD43 and CD34 molecules modified to contain terminal α1,4-linked GlcNAc residues, such compounds thus providing a standard with which to confirm operative linkage of α1,4-linked GlcNAc residues to other carrier molecules.

Two or more polynucleotide sequences also can be operatively linked. For example, a polynucleotide encoding a polypeptide (e.g., a carrier polypeptide) can be operatively linked to a regulatory element (e.g., a mammary gland specific promoter), in which case the regulatory element confers its regulatory effect on the polynucleotide similarly to the way in which the regulatory element would effect a polynucleotide sequence that is normally associated with the regulatory element in a cell (i.e., expression of the encoded polypeptide in a tissue specific manner in mammary epithelial cells). A first polynucleotide coding sequence also can be operatively linked to a second (or more) coding sequence such that two or more polypeptides can be expressed from the operatively linked polynucleotides or, if desired, a chimeric polypeptide can be expressed from the operatively linked coding sequences. Such a chimeric polypeptide can be a fusion polypeptide, in which the two (or more) encoded peptides are translated into a single polypeptide, i.e., are covalently bound through a peptide bond.

The term "carrier molecule" is used herein to refer to a molecule to which one or more α1,4-linked GlcNAc residues can be operatively linked, such that the α1,4-linked GlcNAc residues exhibit *Helicobacter* growth inhibiting activity. As such, a carrier molecule can be a polypeptide, polynucleotide, oligosaccharide, lipid, glycoprotein, nucleotide protein, or the like. Carrier molecules are exemplified herein by an O-glycan (e.g., a core2-branched O-glycan), which can further be operatively linked to a polypeptide (e.g., CD43 or CD34) to generate a glycoprotein.

As disclosed herein, a compound containing one or more α1,4-linked GlcNAc residues can reduce or inhibit one or more of various functions of bacteria that express cholesteryl-α-D-glucopyranoside (CGL), including, for example, growth of the bacteria, motility of the bacteria, or CGL synthesis by the bacteria. The term "reduce or inhibit" means that, in the presence of a compound as disclosed herein, the function be examined is decreased or rendered completely non-functional as compared to level of the function in the absence of the compound. For example, a compound containing one or more α1,4-linked GlcNAc residues is demonstrated herein to reduce or inhibit CGL synthesis in *H. pylori* (see Example 1) as compared to the amount of such synthesis in the absence of the compound. The terms "reduce or inhibit" or "reducing or inhibiting" generally are used together herein because it is recognized that, in some cases, the level of the function can be reduced below a level that can be detected by a particular assay. As such, it may not be determinable using such an assay as to whether, for example, CGL synthesis in *H. pylori* contacted with a composition as disclosed herein is completely inhibited, or whether some level of synthesis that is below the level of detection using a particular assay is maintained. Nevertheless, a decrease from a control level will be detected due to contact with the composition.

*H. pylori*, which is a microaerophilic Gram-negative bacterium that infects the stomach of nearly 50% of the human population, can cause gastric ulcers and is considered a leading cause of gastric malignancies (Marshall and Warren, *Lancet* 1311, 1984; Peek and Blaser, *Nat. Rev. Cancer* 2:28, 2002; Du and Isaccson, *Lancet Oncol.* 3:97, 2002). Most infected individuals remain asymptomatic or are affected merely by chronic active gastritis, and only a fraction of infected patients develop peptic ulcer, gastric cancer, and malignant lymphoma (Cave, *Semin. Gastrointest. Dis.* 12:196, 2001, which is incorporated herein by reference). As such, asymptomatic individuals may have self-defense mechanism. Since *H. pylori* is rarely found in deeper portions of the gastric mucosa expressing O-glycans with terminal α1,4-linked N-acetylglucosamine, these O-glycans were examined to determine whether they can affect *H. pylori* growth.

Gastric mucins are classified into two types based on their histochemical properties (Ota et al., *Histochem. J.* 23:22, 1991, which is incorporated herein by reference). One type of gastric mucin is a surface mucous cell-type mucin that is secreted from the surface mucous cells. The second type of gastric mucin is a gland mucous cell-type mucin found in deeper portions of the mucosa and secreted by gland mucous cells including mucous neck cells, cardiac gland cells, and pyloric gland cells. In gastric mucosa infected with *H. pylori*, microbes are solely associated with surface mucous cell-type mucin, suggesting the presence of carbohydrate ligands for *H. pylori* adhesins in this mucin (Hidaka et al., *Gut* 49:474, 2001). Indeed, carbohydrate structures known as Lewis b and sialyl Lewis X serve as specific ligands for *Helicobacter* adhesin BabA and SabA, respectively, and both carbohydrate ligands are exclusively expressed in the surface mucous cells (Ilver et al., *Science* 279:373, 1998; Mahdavi et al., *Science* 297:573, 2002). In contrast, *H. pylori* rarely colonizes the deeper portions of gastric mucosa producing the gland mucous cell-type mucin, which contains terminal α1,4-linked GlcNAc residues attached to core2-branched O-glycans (GlcNAcα1→4Galβ1→4GlcNAcβ1→6 (GlcNAcα1→4Galβ1→3)GalNAcα→Ser/Thr) (Hidaka et al., supra, 2001). The development of antral atrophy accompanied with loss of gland mucous cells enhances the risk to peptic ulcer or gastric cancer two-fold to three-fold compared with chronic gastritis without antral atrophy (Sipponen and Hyvarinen, *Scand. J. Gastroenterol.* 196 (Suppl. 3):3, 1993, which is incorporated herein by reference). Based on this observation, and knowledge that the majority of *H. pylori*-infected humans are asymptomatic (Cave, supra, 2001), led to an investigation as to whether O-glycans with terminal α1,4-linked GlcNAc expressed in the deeper portion mucin can protect an individual against *H. pylori* infection.

As disclosed herein, O-glycans with terminal α1,4-linked N-acetylglucosamine have antimicrobial activity against *H. pylori*, and inhibit its biosynthesis of cholesteryl-α-D-glucopyranoside, a major cell wall component. Thus a unique subset of O-glycans in gastric mucin can function as a natural antibiotic, protecting the host from the *H. pylori* infection. The identification of these mucins as being protective for *H. pylori* infection has allowed the construction of compounds that are useful for treating or preventing infection by *Helicobacter* species (see Example 1), as well as infection by other bacteria that are characterized, at least in part, by expressing CGL. Accordingly, compositions for treating *Helicobacter* infection are provided, as are methods of making and using such compositions.

In one embodiment, method of producing a glycoprotein containing at least one α1,4-linked GlcNAc residue is provided. In one aspect, the method can be performed, for example, by contacting, under conditions suitable for glycosylation of a polypeptide, an α4GnT, a C2GnT-I, and a carrier polypeptide, which contains at least one O-glycosylation site, whereby the carrier polypeptide is glycosylated by the C2GnT-I or by the C1-β3GnT, and the α4GnT, thereby producing a glycoprotein containing at least one α1,4-linked GlcNAc residue. In a second aspect, the method can be performed using, instead of or in combination with a C2GnT-I, a core 1 extension enzyme such as C1-β3GnT, and a carrier polypeptide that is a substrate for the C1-β3GnT (see, e.g., Yeh et al., *Cell* 105:957-969, 2001, which is incorporated herein by reference). According to this aspect, the carrier polypeptide is glycosylated by the C1-β3GnT, and the α4GnT, thereby producing a glycoprotein containing at least one α1,4-linked GlcNAc residue. The carrier polypeptide can be any polypeptide to which one or more α1,4-linked GlcNAc residues can be attached due to the activity of C2GnT-I (or of C1-β3GnT) and α4GnT, including, for example, a soluble polypeptide (e.g., a soluble CD43 or CD34 polypeptide). Such a method can further include a step of isolating the glycoprotein. As such, a glycoprotein produced by a method of the invention is provided, as is an isolated glycoprotein produced by such a method.

As indicated above, a composition useful for treating or preventing infection of a bacteria that expresses CGL, particularly a *Helicobacter* infection, contain at least one terminal α1,4-linked GlcNAc residue operatively linked to a carrier molecule. Such compositions can be made in vitro or in vivo. For example, a glycoprotein, which comprises a polypeptide carrier molecule containing at least one α1,4-linked GlcNAc residue, can be made by contacting, under conditions suitable for glycosylation of a polypeptide, an α1,4-N-acetylglucosaminyl transferase (α4GnT), a core2 β1,6-N-acetylglucosaminyl transferase-I (C2GnT-I), and a carrier polypeptide, which contains at least one O-glycosylation site. According to this method, the carrier polypeptide is glycosylated by the C2GnT-I and the α4GnT, thereby producing a glycoprotein containing at least one α1,4-linked GlcNAc residue.

Such a glycoprotein also can be produced using recombinant DNA technology. For example, a recombinant glycoprotein containing at least one α1,4-linked GlcNAc residue can be made by expressing in a eukaryotic cell, a polynucleotide encoding an α4GnT, a polynucleotide encoding a C2GnT-I, and a polynucleotide encoding a carrier polypeptide, which contains at least one O-glycosylation site. Generally, one, two or three of the polynucleotides are not otherwise endogenous to the eukaryotic cells and, therefore, one, two or all three encoded polypeptide (i.e., α4GnT, C2GnT-I, and the carrier polypeptide) are heterologous to the eukaryotic cell. Recombinant glycoproteins prepared according to such a method are exemplified herein by a soluble CD43 (leukosialin) molecule modified to contain α1,4-linked GlcNAc residues and by a CD34 modified to contain α1,4-linked GlcNAc residues (see Example 1).

In another embodiment, the present invention relates to non-human transgenic mammal, including female non-human transgenic mammals, which contain one or more transgenes that provide for producing of a recombinant glycoprotein containing one or more α1,4-linked GlcNAc residues, wherein the recombinant glycoprotein can be secreted in milk of the female non-human transgenic mammal. A non-human transgenic mammal of the invention contains, stably integrated in its genome, at least a first exogenous polynucleotide encoding an α4GnT, and, optionally, can contain a second exogenous polynucleotide encoding a C2GnT-I, and/or a third exogenous polynucleotide encoding a carrier polypeptide comprising at least one O-glycosylation site. As disclosed herein, a determination as to whether the transgenic mammal further contains the second and/or third exogenous polynucleotide depends on whether the cell or cells in which a recombinant glycoprotein containing one or more α1,4-linked GlcNAc residues is to be produced naturally express endogenous C2GnT-I and/or the desired carrier polypeptide. For example, mammary epithelial cells naturally produce C2GnT-I and mucin-type glycoproteins. As such, where the transgenic non-human mammal is designed to express the recombinant glycoprotein containing one or more α1,4-linked GlcNAc residues in milk, the transgenic mammal can, but need not, contain a second and/or third exogenous polynucleotide. Accordingly, in various embodiments, a transgenic non-human mammal of the invention contains one, two or all three of the exogenous polynucleotides. In one embodiment, the transgenic non-human mammal contains, stably integrated in its genome, the first exogenous polynucleotide operatively linked to a 5' regulatory sequence of a mammary gland-specific gene including a promoter. In a second embodiment, the transgenic non-human mammal further contains, stably integrated in its genome, the second and/or third polynucleotide, each of which, when present, optionally is operatively linked to a 5' regulatory sequence of a mammary gland-specific gene including a promoter. Further, when present, the third polynucleotide can be operatively linked to a nucleotide sequence encoding a signal sequence effective in directing secretion of the carrier polypeptide into milk.

In still another embodiment, the invention provide a transgenic plant containing, stably integrated in its genome, at least first exogenous polynucleotide encoding an α4GnT; a second polynucleotide encoding a C2GnT-I or encoding a C1-β3GnT; and a third polynucleotide encoding a carrier polypeptide comprising at least one O-glycosylation site, wherein at least one of the first polynucleotide, second polynucleotide, and third polynucleotide is an exogenous polynucleotide; and wherein the first polynucleotide, second polynucleotide, and third polynucleotide are operatively linked to a plant gene 5' regulatory sequence, including a promoter; and whereby, upon expression of the C2GnT-I or the C1-β3GnT, the α4GnT, and the carrier polypeptide, the carrier polypeptide is glycosylated by the C2GnT-I or by the C1-β3GnT, and the α4GnT. The operatively linked promoter, which can comprise a 5' regulatory element that further includes, for example, an enhancer and/or translational regulatory elements, can be a constitutive promoter, an inducible promoter, or a tissue specific promoter, provided that it directs transcription of the encoded polypeptide (e.g., α4GnT) in the desired cells of the plants (e.g., seeds, flowers, leaves, and/or roots). Further, the invention provides seeds produced by such a transgenic plant; products such as grain or flour produced from such a transgenic plant; and products derived from the transgenic plants, seeds, leaves, flowers, or roots of the transgenic plant, or products derived therefrom (e.g., a milk product such as soymilk or rice milk). Methods for producing such products from plants are routine and well known in the art and include, for example, methods of making soymilk (see, e.g., U.S. Pat. Nos. 4,119,733; 4,409,256; 4,902,526; 6,316,043; 6,322,846; and 6,451,359, each of which is incorporated herein by reference) and methods of making rice milk (see, e.g., U.S. Pat. Nos. 4,744,992; 4,894,242; 5,609,895; and 6,599,552, each of which is incorporated herein by reference).

The term "exogenous", when used in reference to a polynucleotide, means that the polynucleotide is not found in a particular cell, or cell of an organism, in nature. The term "heterologous" is used similarly herein, and further can refer to a chimeric polynucleotide comprising two or more nucleotide sequences that are not normally found linked in nature. For example, where a coding sequence of one gene is linked (e.g., operatively linked) a coding sequence of a second gene and/or to a promoter or other regulatory of a second (or other gene), the first coding sequence is heterologous with respect to the second coding sequence and/or regulatory sequence. An exogenous polynucleotide generally is introduced into a cell (e.g., a cell of a non-human embryo) using recombinant DNA methods. Upon expression of the C2GnT-I, α4GnT, and carrier polypeptide in such a transgenic mammal of the invention, the carrier polypeptide is glycosylated by the C2GnT-I and the α4GnT, thereby producing a recombinant glycoprotein containing at least one α1,4-linked GlcNAc residue, which, in a female animal producing milk, can be secreted into the milk.

Methods of making non-human transgenic mammals that secrete a recombinant polypeptide, including a recombinant glycoprotein, into milk are well known (see, for example, U.S. Pat. Nos. 6,344,596; 6,548,735; 6,222,094; 5,962,648; 5,891,698; and 5,850,000, each of which is incorporated herein by reference). As such, the non-human transgenic mammal can be any mammal, including, for example, a mouse, a rat, a rabbit, a horse, a pig, a sheep, a goat, or a cow. In one embodiment, the transgenic mammal is a female non-human transgenic mammal, in which the recombinant glycoprotein can be secreted in an antimicrobially active form into milk produced by the female non-human transgenic mammal.

Accordingly, the invention provides a method for producing an antimicrobial recombinant glycoprotein containing at least one α1,4-linked GlcNAc residue in milk of a female non-human transgenic mammal. The term "antimicrobial", when used herein in reference to a compound containing at least one α1,4-linked GlcNAc residue, means that the compound can reduce or inhibit the growth or function of a bacterium that expresses CGL as compared to the level of growth or of the function in the absence of the compound. A reduction or inhibition in the growth or a function of such a bacterium, e.g., a *Helicobacter* species such as *H. pylori*, can be identified using methods as disclosed herein or otherwise known in the art. For example, antimicrobial activity of a compound can be identified by detecting a decrease in the motility of the bacterium as compared to motility in the absence of the compound, or by detecting decreased number of the bacteria following incubation in a culture medium suitable for growth of the bacteria.

A method of producing such an antimicrobial recombinant glycoprotein in milk of a female non-human transgenic mammal can be performed by 1) introducing into a non-human mammalian embryo at least one of a first polynucleotide encoding α4GnT; a second polynucleotide encoding C2GnT-I; and a third polynucleotide encoding a carrier polypeptide comprising at least one O-glycosylation site, wherein, when fewer than all three polynucleotides is introduced into the embryo, cells of the embryo contain the corresponding endogenous polynucleotide(s), the first polynucleotide, second polynucleotide, and third polynucleotide are operatively linked to a 5' regulatory sequence of a mammary gland-specific gene including a promoter; and wherein the third polynucleotide is operatively linked to a nucleotide sequence encoding a signal sequence effective in directing secretion of the carrier polypeptide into milk; 2) transferring the embryo thereby into a recipient female mammal such that progeny are produced; and 3) inducing milk production in a resulting female progeny containing the first exogenous polynucleotide, second exogenous polynucleotide, and third exogenous polynucleotide operatively linked to the 5' regulatory sequence stably integrated its genome. Milk production can be induced in the female non-human transgenic animal by mating the animal, wherein, as a consequence of pregnancy, milk production is induced in the mammary gland epithelium, or by hormonal treatment of the female non-human transgenic animal such that milk producing is induced. As such, upon expression of the C2GnT-I, α4GnT, and carrier polypeptide in such a female non-human transgenic mammal, the carrier polypeptide is glycosylated by the C2GnT-I and the α4GnT, thereby producing an antimicrobial recombinant glycoprotein comprising at least one α1,4-linked GlcNAc residue, which is secreted into the milk of the female non-human transgenic mammal.

A method of producing a female non-human transgenic mammal, which secretes a recombinant glycoprotein comprising at least one α1,4-linked GlcNAc residue into its milk, can further include a step of milking the female transgenic mammal, thereby obtaining milk containing the recombinant glycoprotein comprising at least one α1,4-linked GlcNAc residue. Further, the method can include isolating the recombinant glycoprotein comprising at least one α1,4-linked GlcNAc residue from the milk, thereby obtaining the recombinant glycoprotein comprising at least one α1,4-linked GlcNAc residue. Accordingly, the invention provides a female non-human transgenic mammal produced by a method of the invention, milk produced from such a female transgenic mammal, and an isolated recombinant glycoprotein comprising at least one α1,4-linked GlcNAc residue obtained from the milk.

The invention provides methods of treating or preventing gastric ulcers due to infection with a *Helicobacter* species. Thus, in one embodiment, the invention provides a method of ameliorating signs or symptoms of a gastric ulcer due to a *Helicobacter* species infection in a subject, by administering to the subject a compound containing at least one α1,4-linked GlcNAc residue, whereby the compound, upon contacting the *Helicobacter*, reduces or inhibits growth of the *Helicobacter* species. In a second embodiment, the invention provides a method of preventing gastric ulcers due to a *Helicobacter* infection in a subject susceptible to such gastric ulcers, by administering to the susceptible subject, a compound containing at least one α1,4-linked GlcNAc residue, whereby the compound prevents *Helicobacter* growth.

As used herein, the term "ameliorate" means that signs or symptoms associated with a gastric ulcer are lessened. The signs or symptoms of gastric ulcers are well known to skilled clinician, as are methods for monitoring the signs and conditions. Symptoms of gastric ulcers can include, for example, a burning pain in abdomen; pain that improves upon eating or the taking of antacids; and pain that gets worse a couple hours after meals. If the ulcer is bleeding, additional symptoms can include vomit that contains bright red blood; or black, tarry bowel movements. Thus, amelioration of a gastric ulcer due to a treatment according to a method of the invention can include, for example, the patient indicating that the pain is reduced. Similarly, the skilled clinician would know that clinical signs of gastric ulcers are lessened, for example, by performing an upper gastrointestinal X-ray following ingestion of liquid barium and detecting a decreased size of the ulcer, or by performing a blood test for anti-*H. pylori* antibodies or for *H. pylori* and measuring a decreased number or absence of the antibodies or bacteria, respectively; or by detecting a decrease or absence of occult blood in a stool sample; or by detecting a decrease in anemia caused by a bleeding gastric ulcer; or by monitoring the gastric mucosa by endoscopy.

*Helicobacter* infection can be detected using any method as disclosed herein or otherwise known in the art. For example, histologic examination using a Steiner modification of the Warthin-Starry silver stain to directly observe spiral bacteria can detect *Helicobacter* by electron microscopy. Microbiologic culture of fecal pellets or cecal smears also can be used to identify *Helicobacter* species using specific media and microaerophilic culture conditions. Polymerase chain reaction (PCR) methods also can be used to detect *Helicobacter* species, and restriction endonucleases can allow differentiation between various *Helicobacter* species.

A subject treated according to a method of the invention can be any subject having or susceptible to having a *Helicobacter* infection in the gastric mucosa. Thus, the subject can be, for example, a mammalian subject, which can be a horse, a pig, a goat, a dog, a cat, a ferret, or the like. In one embodiment, the subject is a human. Correspondingly, the *Helicobacter* species can be any species implicated in the formation of gastric ulcers, including, for example, *H. pylori*, which is implicated in the formation of gastric ulcers in humans. In addition, to *H. pylori*, *Helicobacter* species associated with gastric ulcers include, for example, *H. acinonychis*, which has been isolated from cheetahs with gastritis; *H. aurati*, which has been cultured from gastrointestinal tissues of Syrian hamsters; *H. bizzozeronii*, which has been found in canine stomach; *H. nemestrinae*, which has been found in the stomach of a pigtailed macaque (*Macaca nemestrina*); *H. pametensis*, which has been isolated from bird and swine feces; *H. pullorum*, which has been isolated from poultry and from human patients with gastroenteritis (see *Microbiology*, 140: 3441-3449, 1994); *H. salomonis*, which is a canine gastric *Helicobacter* species related to *Helicobacter felis* and *Helicobacter bizzozeronii* (see J. P. Euzéby, *List of Bacterial Names with Standing in Nomenclature*—Genus *Helicobacter*, which can be found at "http", on the "www", at URL "bacterio.cict.fr/h/helicobacter.html"); *H. mustelae*, which is widespread in the pet ferret population; and *H. heilmannii*, which, like *H. pylori*, infect pigs (see Cantet et al., *Appl. Environ. Microbiol.* 65:4672, 1999). In addition, the compositions and methods of the invention can be used to ameliorate any pathologic condition due to a bacterium that expresses cholesteryl-α-D-glycopyranoside (CGL; Glcα1->cholesterol) as a step of cell wall.

The compound used in a method of the invention can be any compound containing at least one terminal α1,4-linked GlcNAc residue, as disclosed herein, and can be used alone, or in combination with one or more additional therapeutic or nutritional agents that would be recognized by a clinician to be useful in treating an ulcer patient. Thus, the compound can be, for example, a recombinant glycoprotein containing one or more α1,4-linked GlcNAc residues (e.g., a soluble CD43 polypeptide containing terminal α1,4-linked GlcNAc residues), a compound comprising an O-glycan, which contains one or more terminal α1,4-linked GlcNAc residues, or a compound containing gastric gland mucous cell-type mucin, which can be isolated from gastric gland mucosal cells.

A compound to be administered to a subject can be formulated in any manner typical for the type of compound, and can be administered in any convenient way, particularly orally or via intubation such that it is directed to the stomach. For a preventive method, as well as for a therapeutic method, administration is performed by the subject having or susceptible to having a gastric ulcer due to *Helicobacter* infection drinking milk containing the compound, for example, milk obtained from a female non-human transgenic mammal as disclosed herein.

Where the compound is in a form other than in milk, it generally will be formulated in a composition suitable for administration to the subject. As such, the invention provides compositions that include the compound containing at least one terminal α1,4-linked GlcNAc residue, which is useful for preventing or ameliorating gastric ulcers due to a *Helicobacter* infection, and can further contain a pharmaceutically acceptable carrier. As such, the compounds, and compositions containing the compounds, are useful as medicaments for use in treating a subject having or susceptible of having such gastric ulcers.

Pharmaceutically acceptable carriers are well known in the art and include, for example, aqueous solutions such as water or physiologically buffered saline or other solvents or vehicles such as glycols, glycerol, oils such as olive oil or injectable organic esters. A pharmaceutically acceptable carrier can contain physiologically acceptable compounds that act, for example, to stabilize or to increase the absorption of the compound containing at least one terminal α1,4-linked GlcNAc residue (e.g., a recombinant glycoprotein as disclosed herein). Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the physico-chemical characteristics of the therapeutic or preventive compound, and on the route of administration of the composition, which generally is orally, but also can be parenterally such as intravenously, or by injection, intubation, or other such method known in the art. As mentioned above, the composition also can contain a second agent such as a diagnostic reagent, nutritional substance, toxin, or therapeutic agent, for example, an antacid and/or a nutritional supplement.

The total amount of a compound containing the terminal α1,4-linked GlcNAc residue(s) to be administered in practicing a method of the invention will depend on whether the compound is administered for a therapeutic purpose or for a preventive purpose, and can be administered as a single dose or in multiple doses over a prolonged period of time. One skilled in the art would know that the amount of the compound to treat a pathologic condition in a subject depends on many factors including the age and general health of the subject, the route of administration, the number of treatments to be administered, and the severity of the *Helicobacter* infection. In view of these factors, the skilled artisan would adjust the particular dose as necessary and, further, will know that the formulation of the composition and the routes, dose and frequency of administration are determined, initially, using Phase I and Phase II clinical trials.

For oral administration, the compound can be formulated as a tablet, or a solution or suspension form, and can be compounded, for example, with the usual non-toxic, pharmaceutically acceptable carriers for tablets, pellets, capsules, suppositories, solutions, emulsions, suspensions, or other form suitable for use. The carriers, in addition to those disclosed above, can include glucose, lactose, mannose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening or coloring agents and perfumes can be used, for example a stabilizing dry agent such as triulose (see, for example, U.S. Pat. No. 5,314,695).

The present invention also provides a method of reducing or inhibiting cell wall formation of a bacterium that expresses CGL, for example, by contacting the bacterium with a compound containing at least one α1,4-linked GlcNAc residue, whereby CGL synthesis is reduced or inhibited, thereby reducing or inhibiting cell wall formation of the bacterium. As such, the compound can, but need not, reduce or inhibit UDP-Glc:sterol glucosyltranserase activity in the bacterium as a means of reducing or inhibiting CGL synthesis. Accordingly, the invention also provides a method of reducing or inhibiting growth of bacteria expressing CGL, for example, by contacting the bacteria with a compound containing at least one I1,4-linked GlcNAc, whereby CGL synthesis is reduced or inhibited, thereby reducing or inhibiting growth of the bacterium. The method can be performed by contacting the bacteria in vitro, for example, by adding the compound to bacteria cells in culture, or by contacting the bacteria in vivo, for example, by directing the compound to the stomach of a subject infected with the bacteria, for example, a mammal infected with a *Helicobacter* species such as a human infected with *H. pylori*.

The following examples are intended to illustrate but not limit the invention.

EXAMPLES

In an α-MEM medium containing 10% fetal calf serum (FCS), Chinese hamster ovary cell mutant (CHO.Lec2 cells) deficient in a CMP-sialic acid transporter was cultured. By amplifying a DNA fragment (a portion corresponding to the 20th to 254th amino acids of the amino acid sequence of SEQ ID NO:1, including the whole extracellular domain of the CD43 by the PCR method and subcloning the amplified DNA fragment into pSecTag2 (product of Invitrogen), Igκ leader peptide, myc epitope following it and a vector (pSecTag2-sCD43) encoding $(His)_6$ were produced. Then, four vectors having, incorporated in the pSecTag2-sCD43, (1) cDNA encoding core 2β1,6-N-aceteylglucosaminyl transferase-I (C2GnT-I), (2) cDNA encoding α1,4-N-acetylglucosaminyl transferase (α4GnT), and (3) cDNA encoding a polyoma virus large T antigen, respectively are transfected into the cultured CHO.Lec2 cells using LipofectAmine™ reagent (Invitrogen Corp.) to cause expression of soluble CD43 containing a terminal GlcNAcα residue in the transfected CHO.Lec2 cells, whereby the GlcNAcα-CD43 was produced.

The GlcNAcα-CD43 thus produced were subjected to measurement of GlcNAcα-CD43 activity with a commercially available ELISA kit (ELISA kit for gastric gland mucous cell-type mucin measurement, available from Kanto Kagaku) using an HIK1083 antibody (HIK1083 latex for gastric mucin detection, available from Kanto Kagaku) specific to the GlcNAcα residue (See, for example, A new diagnostic method for adenoma malignum and related lesions: latex agglutination test with a new monoclonal antibody (HIK1083; Clinica Chimica Acta 312 (2001) 231-233). For coloring reaction, ELISA ELAST amplification system (Perkin Elmer) was used. Coloring was observed, and the expression of a terminal GlcNAcα residue was confirmed. Further, quantification of protein was performed using a commercially available quantification system (BCA Protein Assay Kit, Pierce Biotechnology, Inc., Cat No. 23225, 23227). As a result, it was revealed that the number of the side chains (sugar chains) of the GlcNAcα-CD43 relative to each main chain (CD43) was 80 and that the sugar chains exist in the cluster form relative to the main chain. Additional analysis of the sugar chain using another commercially available quantification kit (Glycoprotein Carbohydrate Estimation Kit, Pierce Biotechnology, Inc., Cat No. 23260) revealed that the sugar chain is formed of GlcNAcα1→4Galβ1→4GlcNAβ1→6 (GlcNAcα1→4Galβ1→3)GalNAcα→Ser/Thr; its branch number of the sugar chain is 1; and the number of monomer units is 6. The term "Ser/Thr" means bonding to either one of serine (Ser) or threonine (Thr) in CD43 serving as the main chain.

The transfected CHO.Lec2 cells succeeded in efficient synthesis of the CD43 by the polyoma.virus large T-antigen. The cDNA encoding the α4GnT was produced in accordance with the method as described in JP-A No. 2001-46077. Production of CD43 free of an α type N-acetylglucosamine residue was as follows. For the measurement of control, soluble CD43 having no GlcNAcα residue in a core 2 branched O-glycan was produced in a similar manner to that employed for the production of the GlcNAcα-CD43 except for the use of a pcDNAI vector (Invitrogen) not having cDNA of the α4GnT incorporated therein. The GlcNAcα-free CD43 thus produced were subjected to condensation reaction using a latex particle antibody specific to the GlcNAcα residue. No condensation was observed. As a result, it was revealed that the GlcNAcα-free CD43 did not contain a GlcNAcα residue. A further analysis of sugar chains revealed that the side chain (sugar chain) of CD43 not containing the GlcNAcα is formed of Galβ1→4GlcNAcβ1→6(Galβ1→3)GalNAcα→Ser/Thr. The "Ser/Thr" means bonding to either one of serine (Ser) or threonine (Thr) in CD43 serving as the main chain.

The growth, motility and abnormal morphologies of bacteria, and suppression or inhibition of CGL biosynthesis by a GlcNAcα residue were evaluated in the below-described manners by using the GlcNAcα-residue-containing soluble CD43, and GlcNAcα-residue-free CD43. Growth of bacteria was as follows. By the microbroth dilution method, Helicobacter pylori (ATCC43504) was pre-cultured on a Brucella medium (Becton Dickinson Microbiology Systems) containing 10% horse serum. The H. pylori diluted to $1 \times 10^7$ cells/ml and GlcNAcα-CD43 having the concentration as shown in FIG. 2A was charged in a 96-well plate, followed by culturing for 4 days under conditions of 35° C. and 15% $CO_2$. In FIG. 2A, "αGlcNAc (+)" means that the GlcNAcα-CD43 is contained in the medium, while "αGlcNAc (−)" means that the soluble CD free of a GlcNAcα residue is contained in the medium. The concentration of the soluble CD free of a GlcNAcα residue in the medium is 125.0 mU/ml. Growth of the H. pylori thus cultured was measured under the condition of OD600 nm by using a microplate spectrophotometer (SPECTRAmax PLUS 384 spectrophotometer; Molecular Device). The results are shown in FIG. 2A. The minimum inhibitory concentration was measured in a similar manner to that employed above except for the use of Muller Hinton medium (product of Eiken Chemical) instead of the Brucella medium, whereby similar results were produced.

As a result, as illustrated in FIG. 2A, growth for the first 2.5 days was slight irrespective of the presence or absence of the GlcNAcα residue, which is a characteristic of the growth induction period of H. pylori. On Day 3 after incubation, the growth period started and drastic growth of H. pylori was observed on the medium containing the soluble CD43 free of the GlcNAcα residue. It has been proved that growth of H. pylori was suppressed or inhibited by the incubation with the GlcNAcα-CD43. The unit "1 mU" is equivalent to 1 µg of p-nitrophenyl-N-acetylglucosamine (GlcNAcα-PNP). Motility of bacteria was measured as follows. On a Brucella medium containing 31.2 mU/ml of GlcNAcα-CD43. H. pylori was cultured for 3 days. In order to study the motility of the H. pylori thus cultured, a time-lapse photograph of it was taken at an interval of 1 second through a confocal laser scanning microscope ("LSM510 META", product of Carl Zeiss) and the typical H. pylori was indicated by an arrow. The result is shown in Table 1B. A photograph was taken in a similar manner except for the use of a Brucella medium containing the soluble CD43 free of a GlcNAcα residue (results shown in Table 1A, below).

In FIG. 2B, "αGlcNAcα (+)" means that the GlcNAcα-CD43 is contained in the medium, while "αGlcNAcα (−)" means that the soluble CD43 free of a GlcNAcα residue is contained in the medium. In each case, its concentration is 31.2 mU/ml. The underline on the right bottom of FIG. 2B represents 50 µm and all the pictures are time-lapse photographs taken at equal magnifications.

As a result, an average velocity of seven H. pylori cultured on the GlcNAcα-CD43-containing medium (αGlcNAcα (+)) was 3.1±3.5 µm/sec, while that of seven H. pylori cultured on the medium (αGlcNAcα (−)) containing the CD43 free of a GlcNAcα residue was 21.1±2.6 µm/sec. The significance by a t test was P<0.001. Accordingly, it has been found that the motility of H. pylori decreases drastically on the GlcNAcα-CD43-containing medium.

Abnormal morphologies of bacteria were detected. On a Brucella medium containing the GlcNAcα-CD43 or the soluble CD43 free of a GlcNAcα residue at a concentration of 31.2 mU/ml, H. pylori was cultured for 3 days. The SEM photograph of the H. pylori thus cultured was taken under the condition of accelerating voltage of 15 kV by using a scanning electron microscope ("JSM-6360LV", product of JEOL; see Table 1C). In Table 1C (below), "αGlcNAc (+)" means that the GlcNAcα-CD43 is contained in the medium, while "αGlcNAc (−)" means that the soluble CD43 free of a GlcNAcα residue is contained in the medium. In each case, its concentration is 31.2 mU/ml. The underline on the right bottom of FIG. 2C represents 1 µm and all the pictures are SEM photographs taken at equal magnifications. As a result, abnormal morphologies such as elongation, narrowing and bending were observed in *H. pylori* cultured on the GlcNAcα-CD43-containing medium (αGlcNAcα (+)), while no abnormal morphologies were observed from the *H. pylori* cultured on the medium containing CD43 free of a GlcNAcα residue (αGlcNAcα (−)).

Inhibition of CGL biosynthesis was determined. The inhibition of CGL biosynthesis by the GlcNAcα residue was analyzed in the below-described manners in two cases, that is, (1) CGL biosynthesis of *H. pylori* in vivo and (2) CGL biosynthesis in vitro. Inhibition of CGL biosynthesis of *H. pylori* in vivo was determined, as was synthesis of CGL by *H. pylori* in the presence of GlcNAcα-CD43. By using cholesterol and UDP-glucose, CGL was synthesized by *H. pylori* in the presence of GlcNAcα-CD43. The CGL thus biosynthesized in *H. pylori* in vivo was subjected to MALDI-TOF mass analysis. After pre-culturing of *H. pylori* (ATCC43504) on a *Brucella* medium (Becton Dickinson Microbiology Systems) containing 10% horse serum, the *H. pylori* diluted to $1 \times 10^7$ cells/ml and GlcNAcα-CD43 adjusted to have a concentration of 4.0 mU/ml were charged in a 96-well plate, followed by culturing for 2 days at 35° C. The *H. pylori* thus cultured were collected, washed three times with PBS (free of $Ca^{2+}$ and $Mg^{2+}$), and suspended in 1 ml of distilled water. The resulting suspension was centrifuged for 10 minutes at 6000 rpm, whereby cells were obtained. The resulting cells were extracted overnight at 4° C. in 2 ml of a chloroform.methanol mixture (2:1, by mass) mixture. The extract was filtered, followed by drying in a nitrogen gas stream. The dried sample thus obtained was dissolved in 4 ml of a chloroform.methanol mixture (2:1, by mass).

In accordance with the process for Folch et al., 1 ml of water was added to the solution. The lower phase of the resulting mixture was dried in a nitrogen gas stream and then, treated with 1 ml of a 0.5N sodium hydroxide.methanol solution for 1 hour at 50° C. After neutralization with a 6N aqueous solution of hydrochloric acid, 1 ml of petroleum ether was added to a reaction tube. After removal of the upper phase, 2 ml of petroleum ether was added to the lower phase. The lower phase was dried and then dissolved in 1 ml of a chloroform.methanol.water mixture (86:14:1, by mass) (TLP). To the same reaction tube, 0.5 ml of another chloroform.methanol.water mixture (3:48:47, by mass) (TUP) was added. From the resulting mixture, the lower phase was collected, dried in a nitrogen gas stream and then dissolved in 50 μl of chloroform. In the next place, 1 μl of the sample was weighed, followed by the addition of 1 μl of 2,5-dihydroxybenzoic acid or 1 μl of trans-3-indoleacrylic acid. The resulting mixture was employed as a matrix. The mass spectrum of the sample was measured using Voyager-DE STR Biospectrometry Workstation DE MALDI-TOF MS (product of PE Applied Biosystems) in a positive ion or negative ion reflector mode at laser intensity of 2300. External calibration with 2 points was conducted with phosphatidic acid internally appearing in *H. pylori* as an internal standard. The results are shown in FIG. 2B.

Figure 3:
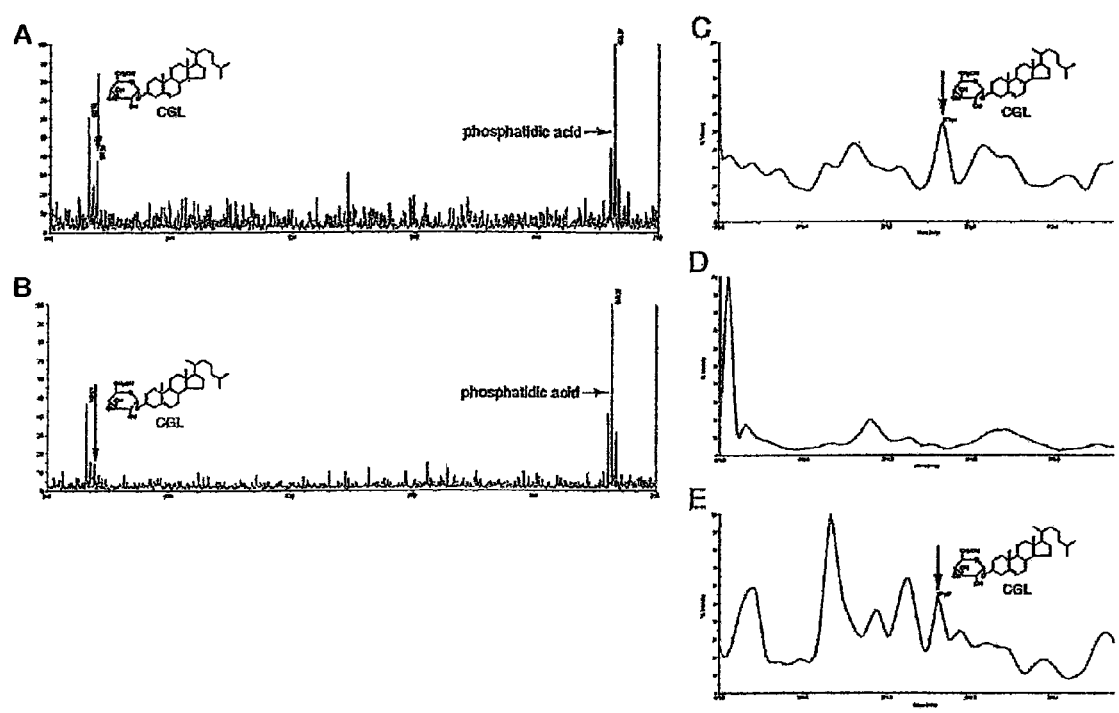
FIGS. 3A to 3E show that soluble CD43 with terminal α1,4-linked GlcNAc residues suppresses cholesteryl-α-D-glucopyranoside (CGL) biosynthesis in *H. pylori* in vivo (FIGS. 3A and 3B) as well as in vitro (FIGS. 3C to 3E) as determined by MALDI-TOF mass spectrum.

As a control, the mass spectrum of CGL was measured in a similar manner except for the use of the CD43 free of a GlcNAcα residue instead of the GlcNAcα-CD43. The results are shown in FIG. 3A. As shown in FIGS. 3A and 3B, a peak of CGL was detected at m/z of 571.6 both in the presence of the GlcNAcα-CD43 and in the presence of the CD43 free of a GlcNAcα residue. The peak of CGL in the presence of the GlcNAcα-CD43 however showed a drastic decrease to 29.5% compared with the peak of CGL measured in the control. These results demonstrate that the GlcNAcα-CD43 inhibited biosynthesis of CGL in *H. pylori* in vivo.

Inhibition of biosynthesis of CGL was determined in vitro, as was synthesis of CGL by *H. pylori* in the presence of GlcNAcα-CD43. By using cholesterol and UDP-glucose, CGL was synthesized by sonicated *H. pylori* and MALDI-TOF mass spectrometry of the CGL synthesized in vitro was performed in the below-described manner. After pre-culturing of *H. pylori* (ATCC43504) on a *Brucella* medium (Becton Dickinson Microbiology Systems) containing 10% horse serum, the *H. pylori* diluted to $5 \times 10^7$ cells/ml was cultured on a *Brucella* medium added with 5% horse serum at 35° C. for 2 days. A 2 ml portion of the *H. pylori* ($5 \times 10^7$ cells/ml) thus cultured was collected, washed three times with PBS (free of $Ca^{2+}$ and $Mg^{2+}$), and suspended in 1 ml of distilled water. The resulting suspension was centrifuged for 10 minutes at 6000 rpm, whereby a lipid component was obtained.

In 1 ml of a reaction buffer containing 100 mM Tris buffer (pH 7.5), 15 mass % of glycerol, 5 mM DTT, 200 μM Pefabloc (product of Merck) and 0.5 mg/ml of lysozyme, *H. pylori* was suspended, followed by culturing at 20° C. for 5 minutes. On an ice bath, the sample was sonicated 10 times in an ultrasonic water bath at intervals of 30 seconds. Then, 100 μl of a reaction mixture containing 80 μl of the sonicated *H. pylori*, 5 μl of a 8 mM cholesterol ethanol solution, 5 μl of 7.2 μM UDP-Glc (UDP-glucose), 1 μl of Triton CF-54 detergent (Sigma Chemical Co., St. Louis, Mo., USA) and 9 μl of the reaction buffer was allowed to stand (incubated) at a fixed temperature of 30° C. for 3 hours. The reaction was then terminated by the addition of 900 μl of a 0.45% NaCl solution and 4 ml of a 2:1 chloroform:methanol mixture.

From the resulting mixture, the lower phase was filtered, followed by drying in a nitrogen gas stream. The lipid sample thus obtained by drying was dissolved in 4 ml of a chloroform.methanol mixture (2:1, by mass). In accordance with the process for Folch et al., 1 ml of water was added to the solution. The lower phase of the resulting mixture was dried in a nitrogen gas stream and then, treated with 1 ml of a 0.5N sodium hydroxide-methanol solution for 1 hour at 50° C. After neutralization with a 6N aqueous solution of hydrochloric acid, 1 ml of petroleum ether was added to a reaction tube. The upper phase was removed and then, 2 ml of petroleum ether was added to the lower phase. The lower phase was dried and then dissolved in 1 ml of a chloroform.methanol.water mixture (TLP) (86:14:1, by mass). To the same reaction tube, 0.5 ml of another chloroform-methanol-water mixture (TUP) (3:48:47, by mass) was added. From the resulting mixture, the lower phase was collected, dried in a nitrogen gas stream and then dissolved in 50 μl of chloroform.

In the next place, 1 μl of the sample was weighed, followed by the addition of 1 μl of 2,5-dihydroxybenzoic acid or 1 μl of trans-3-indoleacrylic acid. The resulting mixture was employed as a matrix. The mass spectrum of CGL was measured using Voyager-DE STR Biospectrometry Workstation DE MALDI-TOF MS (product of PE Applied Biosystems) in a positive ion reflector mode at laser intensity of 2500. External calibration with 2 points was conducted with phosphatidic acid internally appearing in *H. pylori* as an internal standard. The results are shown in FIG. 3C.

In a similar manner to that employed above except that 5.0 mU of GlcNAcα-CD43 was added to the reaction buffer, the mass spectrum of CGL was measured. The results are shown in FIG. 3D. Further, in a similar manner to that employed above except that 5.0 mU of CD43 free of a GlcNAcα residue was added to the reaction buffer, the mass spectrum of CGL was measured. The results are shown in FIG. 3E.

The sample synthesized by the sonicated *H. pylori* by using UDP-Glc and cholesterol was subjected to MALDI-TOF mass spectrometry, resulting in the detection of a peak of CGL at m/z of 571.6 as is apparent from FIG. 3C. This result can occur because *H. pylori* has an activity of UDP-Glc:sterol glucosyltransferase for transferring UDP-Glc to the C3 position of cholesterol as illustrated in the below-described scheme.

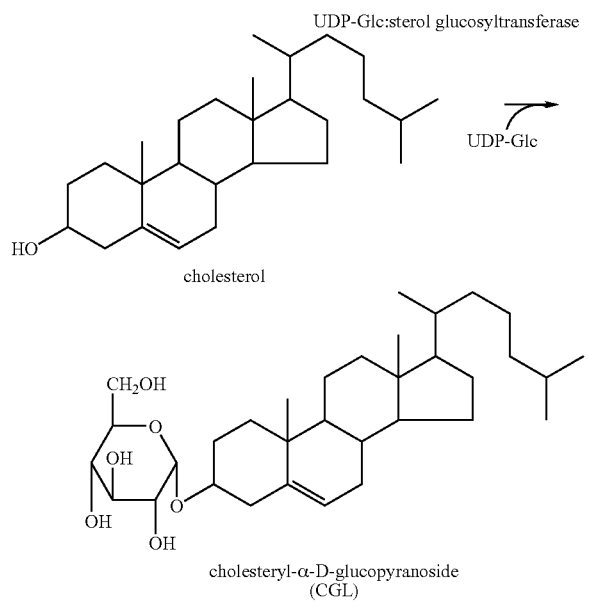

No peak of CGL was however detected at m/z of 571.6 as illustrated in FIG. 3D when incubation was conducted similarly in the presence of the GlcNAcα-CD43. When incubation was conducted in a similar manner in the presence of the CD43 free of a GlcNAcα residue instead of the GlcNAcα-CD43, a peak of CGL was detected at m/z of 571.6, and not difference was found from the peak of CGL when neither the GlcNAcα-CD43 nor the CD43 free of a GlcNAcα residue was added. These results demonstrate that the GlcNAcα residue inhibited biosynthesis of CGL.

The formation mechanism of the cell walls of *H. pylori* including identification of glycosyltransferase relating to the biosynthesis of α-CGS has not yet been elucidated. In consideration of the similarity in structure of the GlcNAcα residue and α-binding type Glc contained in CGL, however, the above-described analysis results suggest that biosynthesis of CGL may be inhibited by the competition between the GlcNAcα residue and UDP-Glc for a donor substrate of UDP-Glc:sterol glycosyltransferase or by the direct inhibition against UDP-Glc:sterol glycosyltransferase by the final product inhibiting mechanism of the GlcNAcα residue. Based on the evaluation results of growth, motility, appearance of abnormal morphologies of bacteria and suppression or inhibition of CGL biosynthesis by the GlcNAcα residue, it has been understood that administration of a functional molecule having an α1,4-acetylglucosamine residue alleviates or prevents the signs or symptoms of gastric ulcer or gastric cancer induced by the infection of subjects with *Helicobacter* bacteria.

Tests were performed to examine the survival of *H. pylori* in the presence or absence of cholesterol and synthesis of CGL by *H. pylori*. Surviving condition of *H. pylori* in the presence or absence of cholesterol was determined. Genes relating to the biosynthesis of cholesterol have not yet been discovered from the genomic data of *H. pylori*. Considering the possibility that *H. pylori* cannot synthesize CGL without exogenous cholesterol, the following test was conducted. Described specifically, when *H. pylori* (ATCC43504) was cultured on an Ham's F-12 medium free of cholesterol for 5 days under the standard anaerobic conditions at 35° C., growth of *H. pylori* was suppressed to the level of 50% of that cultured on an Ham's F-12 medium containing cholesterol under similar conditions. The results are shown in Table 1.

*H. pylori* did not show motility on the cholesterol-free medium but abnormal extension (abnormal morphology) was observed as is apparent from the left side of FIG. 2C. The *H. pylori* died out completely when cultured for further 21 days in the absence of cholesterol. When cultured on a cholesterol-added medium, on the other hand, *H. pylori* growth was smooth and no abnormal morphology was discovered (Table 1). It has been understood from these results that synthesis of CGL using cholesterol is necessary for the survival of *H. pylori*.

Figure 4:
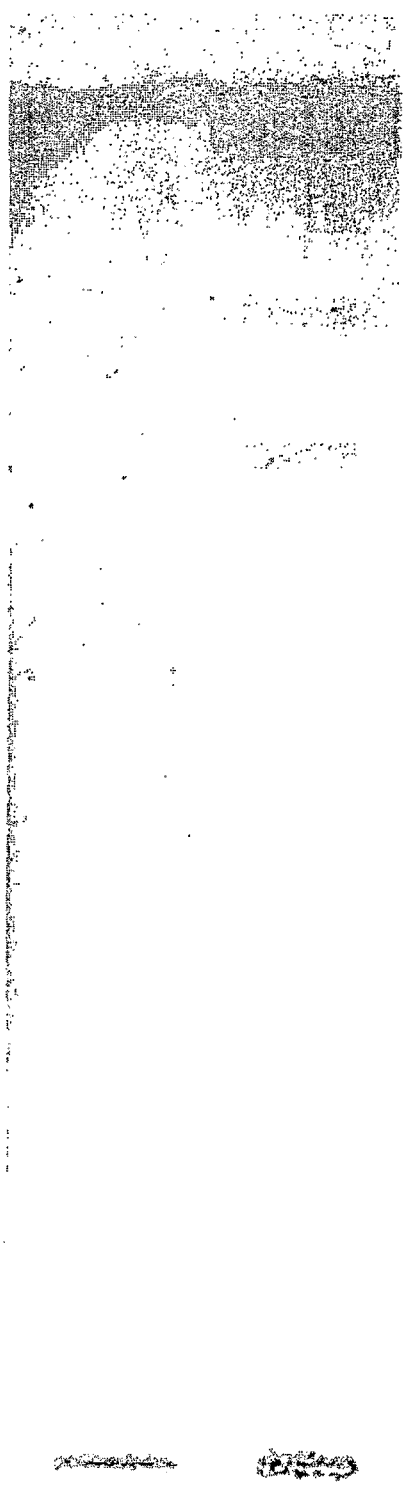
FIG. 4 demonstrates an absence of CGL in *H. pylori* cultured in the absence of cholesterol. Total glycolipids extracted from 1×10$^8$ cells of *H. pylori* incubated with *Brucella* broth lacking cholesterol (lane 1) or containing 0.005% cholesterol (lane 2) were analyzed by TLC. The solvent system used was chloroform-methanol-water (16:6:1), and the glycolipids were visualized using orcinol-containing sulfuric acid. CAG, cholesteryl-6-O-tetradecanoyl-α-D-glucopyranoside; CGL, cholesteryl-α-D-glucopyranoside; CPG, cholesteryl-6-O-phosphatidyl-α-D-glucopyranoside.

Synthesis of CGL by *H. pylori* was determined. The expression level of CGL in *H. pylori* in the presence or absence of cholesterol was studied by analyzing, as described below, variations in the expression level of αCGs containing CGL at the glycolipid portion of *H. pylori* through thin-film chromatography (TLC). From a *Brucella* medium containing cholesterol and a cholesterol-free medium on each of which *H. pylori* had been cultured, 1×10⁸ cells/ml of *H. pylori* were collected and the glycolipid portion thereof was extracted over 1 hour at room temperature by using a 2:1 (mass ratio) mixture of chloroform and methanol. The extract was dried under a nitrogen gas stream, followed by thin-film chromatography (TLC) with a 16:6:1 (mass ratio) mixture of chloroform, methanol and water. The glycolipid portion thus separated was visualized by staining with an orcinol sulfate buffer at 110° C. The results are shown in FIG. 4, wherein Lane 1 shows the analysis results of the glycolipid portion extracted from *H. pylori* cultured on a cholesterol-free *Brucella* medium, while Lane 2 shows the analysis results of the glycolipid portion extracted from *H. pylori* cultured on a cholesterol-containing *Brucella* medium. As a result, three adjacent lines typical of CGL-containing α-CGs, which lines are characteristic of *H. pylori*, were detected when *H. pylori* was cultured on a cholesterol-containing medium (Lane 2). On the other hand, no α-CGs (CGL) was detected when *H. pylori* was cultured on a cholesterol-free medium (Lane 1).

Production of CD34 containing an α type N-acetylglucosamine residue was examined. In a similar manner as described above (see, also, Example 1, below) except that pcDNA3 (Invitrogen) was used instead of pSecTag2, and pcDNA3-CD34-IgG encoding soluble CD34-IgG chimera was used instead of cDNA encoding soluble CD43, soluble CD34 containing a GlcNAcα residue was produced. The growth, motility and appearance of abnormal morphologies of bacteria were analyzed and inhibition of CGL biosynthesis by the GlcNAcα residue was evaluated as described above, and similar results were obtained (see Example 1, below).

Production of AGS cells expressing CD43 containing an α type N-acetylglucosamine residue was examined. In a similar manner to that described above (see, also, Example 1, below) except for the use of gastric adenocarcinoma cells (AGS cells) instead of CHO.Lec2 cells, AGS-α4GnT cells stably expressing GlcNAcα-CD43 were produced. Production of AGS cells expressing CD43 not containing an α type N-acetylglucosamine residue. In a similar manner to that employed for the production of AGS-α4GnT cells except that a pcDNAI vector (product of Invitrogen) having the α4GnT-encoding cDNA not incorporated therein was used, Mock-transfected AGS cells stably expressing CD43 not containing a GlcNAcα residue was produced for the measurement of control. The AGS-α4GnT cells or Mock-transfected AGS cells thus produced were co-cultured with 1×10⁷ cells/ml of *H. pylori* ( ) for 24 hours. The cells thus cultured were photographed by a Nomarski microscope. The results are shown in the lower part of FIG. 5.

After immobilization with 20% buffer formalin, the AGS-α4GnT cells or Mock-transfected AGS cells were incubated together with a mixture of a rabbit polyclonal antiserum (DAKO) against *H. pylori* and mouse monoclonal HIK1083 antibody (product of Kanto Chemical), followed by fluorescent staining with the mouse monoclonal HIK1083 antibody. As the secondary antibody, rhodamine-labeled anti-rabbit immunoglobulin (for anti-*H. pylori* antibody) and fluorescein isothiocyanate-labeled antimouse IgM (for HIK1083 antibody) were added and a slide was made. The slide was sealed with Vectashield (product of Vector Laboratories) and photographed by a confocal laser scanning microscope ("LSM510 META", product of Carl Zeiss). The results are shown in the upper part of FIG. 5.

Figure 5:
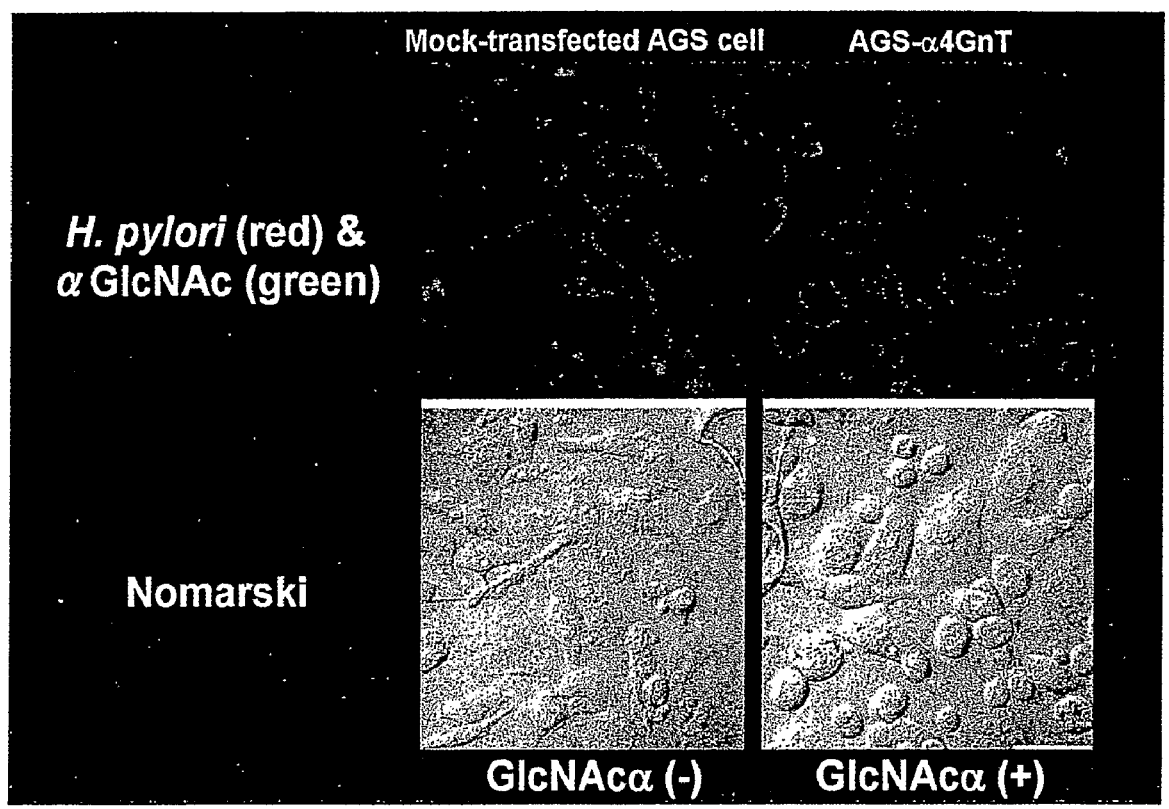
FIG. 5 shows that O-glycans with terminal α1,4-linked GlcNAc protect gastric adenocarcinoma cells from cell damage caused by *H. pylori*. Note that a large number of *H. pylori* adhered to AGS cells transfected with vector alone, resulting in marked cellular damage such as cell flatness or shrinkage (arrows). On the other hand, *H. pylori* adhered poorly to AGS-α4GnT cells stably transfected with α4GnT, and no cellular damage was noted in these cells. Double immunohistochemistry of AGS cells with anti-*H. pylori* antibody (red) and HIK1083 antibody (Ishihara et al., *Biochem. J.* 318:409, 1996, which is incorporated herein by reference) specific for terminal α1,4-linked GlcNAc (green). Nomarski photographs of the same field are shown in the lower panel. Bar=50 Tm.

On the upper right of FIG. 5, shown is a photograph of the fluorescent-stained AGS-α4GnT cells. A portion in white represents the fluorescent-stained HIK1083 antibody and it has been confirmed that the HIK1083 antibody surrounds the AGS-α4GnT cells. The HIK1083 antibody is specific to the GlcNAcα residue, suggesting the expression of the GlcNAcα residue by the AGS-α4GnT cells. As illustrated in the lower right of FIG. 5, no cellular damage was observed in the AGS-α4GnT cells in which the GlcNAcα residue has been expressed.

In the upper left of FIG. 5, shown is a photograph of the Mock-transfected AGS cells which were fluorescent-stained in a similar manner to that employed for the AGS-α4GnT cells. A portion in white represents *H. pylori* and it has been confirmed that *H. pylori* exists to surround the Mock-transfected AGS cells and that the GlcNAcα residue has not been expressed because of the absence of the fluorescent-stained HIK1083 antibody. As illustrated in the lower left of FIG. 5, remarkable cellular damage was observed in the AGS-α4GnT cells in which no GlcNAcα residue has been expressed.

According to a known process of enzyme synthesis (see, e.g., Murata and Usui, Trends Glycosci. Glycotech., 12, 161-174, 2000), a sugar chain consisting of 6 residues, GlcNAcα1→4Galβ1→4GlcNAcβ1→6 (GlcNAcα1→4Galβ1→3)GalNAcα, was produced. In a similar manner to that described above (see, also, Example 1, below), growth, motility and appearance of abnormal morphologies of bacteria were analyzed and inhibition of CGL biosynthesis by a GlcNAcα residue were evaluated, whereby similar results to those described above were obtained (see, also, Example 1).

These results demonstrate that CGL is required for the growth of *H. pylori* and that the GlcNAcα residue exhibits an antibacterial property against *H. pylori* by inhibiting biosynthesis of CGL.

EXAMPLE 1

O-Glycans Containing Terminal α1,4-Linked N-acetylglucosamine have Antimicrobial Activity This example demonstrates that O-glycans produced in gastric gland mucous cell-type mucin act as a natural inhibitor of *Helicobacter pylori* growth, and that synthetic compositions containing terminal α1,4-linked N-acetylglucosamine have antimicrobial activity.

Materials and Methods

Bacterial Strains

Standard strain of *H. pylori* (ATCC43504) was purchased from American Type Culture Collection ("ATCC"; Manassas Va.) and used for the experiments shown in this report. Additional bacterial strains used for cell growth assay were as follows: *H. pylori* (ATCC43526) purchased from ATCC and clinical isolates of *H. pylori* (#749, #750, and #751), *Escherichia coli*, *Pseudomonas aeruginosa*, *Klebsiella pneumoniae*, *Staphylococcus aureus*, I-*Streptococcus*, and *Streptococcus pneumoniae*. All clinical isolates were characterized in the Department of Laboratory Medicine, Shinshu University Hospital, Japan.

Production of Soluble CD43 with or without α1,4-linked GlcNAc Residues

A mutant Chinese hamster ovary Lec2 cell line defective in CMP-sialic acid transporter (Deutscher et al., *Cell* 39:295, 1984, which is incorporated herein by reference) was maintained in α-MEM supplemented with 10% fetal calf serum. A DNA fragment containing the entire extracellular domain of CD43 (amino acid residues 20 to 254) was amplified by PCR and subcloned into the pSecTag2 vector (Invitrogen; Carlsbad Calif.), encoding an IgP leader peptide followed by a myc epitope and (His)₆ (pSecTag2-sCD43). Lec2 cells were transfected by cDNAs encoding C2GnT-I (Bierhuizen and Fukuda, *Proc. Natl. Acad. Sci., USA* 89:9326, 1992, which is incorporated herein by reference), α4GnT (Nakayama et al., *Proc. Natl. Acad. Sci., USA* 96:8991, 1999, which is incorporated herein by reference), and soluble CD43 together with polyoma large T antigen cDNA using LipofectAmine™ reagent (Invitrogen). The polyoma large T antigen allowed transfected Lec2 cells to efficiently produce recombinant proteins (Bierhuizen and Fukuda, supra, 1992).

Soluble CD43 without terminal α1,4-linked GlcNAc residues on core2-branched O-glycans was prepared using pcDNAI vector (Invitrogen) without a cDNA insert instead of α4GnT cDNA, and used as a control. After one week, soluble CD43 released into the medium (α-MEM supplemented with 10% fetal calf serum) was concentrated using CENTRIPREP YM-30 filter (Millipore: Bedford Mass.) and used for the assay. Activity of soluble CD43 with terminal α1,4-linked GlcNAc was determined using a commercial ELISA kit and HIK1083 antibody specific for terminal α1,4-linked GlcNAc (Kanto Kagaku; Tokyo, Japan; Ishihara et al., *Biochem. J.* 318:409, 1995, which is incorporated herein by reference); the color reaction was developed with an ELAST ELISA amplification system (Perkin Elmer; Boston Mass.). In this assay, one unit was defined as immunoreactivities equivalent to 1 mg (2.9 Tmoles) of p-nitrophenyl-N-acetyl-α-glucosaminide (GlcNAcα-PNP) according to the manufacturer's instructions. Protein concentrations of these recombinants were measured using BCA protein assay (Pierce; Rockford Ill.). Similarly, soluble CD34 proteins with or without terminal α1,4-linked GlcNAc were produced using pcDNA3-CD34-IgG (Yeh et al., *Cell* 104:957, 2001, which is incorporated herein by reference) encoding a soluble CD34-IgG chimera instead of pSecTag2-sCD43 vector.

Cell Growth Assay

*H. pylori* was precultured in *Brucella* broth (Becton Dickinson Microbiology Systems; Sparks Md.) supplemented with 10% horse serum according to a microbroth dilution method (Piccolomini et al., *J. Clin. Microbiol.* 35:1842, 1997, which is incorporated herein by reference). The diluted bacteria (1×10⁷ cells/ml) were cultured with *Brucella* broth supplemented with 5% horse serum containing various amounts of soluble CD43 with or without terminal α1,4-linked GlcNAc in 96-well plates at 35° C. under 15% $CO_2$ for 4 days. Bacterial growth was measured at OD 600 nm using a microplate SPECTRA max PLUS384 spectrophotometer (Molecular Devices; Sunnyvale Calif.). Similarly, the minimum inhibitory concentrations were determined using a microbroth dilution method with Mueller-Hinton broth (Eiken Chemical, Tokyo, Japan) instead of Brucella broth.

Cell Motility Assay

Cell motility of H. pylori incubated in Brucella broth containing 31.2 mU/ml of soluble CD43 with terminal α1,4-linked GlcNAc or the same protein concentration of soluble CD43 without terminal α1,4-linked GlcNAc for 3 days was evaluated by taking time-lapse images at 1 sec-intervals using a laser confocal microscope LSM510 META (Carl Zeiss, Jena, Germany).

Scanning Electron Microscopy

Scanning electron micrographs of H. pylori cultured with Brucella broth containing 31.2 mU/ml of soluble CD43 with terminal α1,4-linked GlcNAc or the same protein concentration of soluble CD43 without terminal α1,4-linked GlcNAc for 3 days were obtained by a scanning electron microscope JSM-6360LV (JEOL, Tokyo, Japan) at 15 kV accelerating voltage.

Detection of CGL by Mass Spectrometry

After preculture of H. pylori in Brucella broth supplemented with 10% horse serum, $1\times10^7$ cells/ml of the microbes were incubated with Brucella broth containing 5% horse serum and 4.0 mU/ml of soluble CD43 with terminal α1,4-linked GlcNAc or the same protein concentration of soluble CD43 without terminal α1,4-linked GlcNAc at 35° C. for 2 days. H. pylori was harvested, washed in PBS ($Ca^{2+}$, $Mg^{2+}$ free) three times, and resuspended in 1 ml of distilled water. After centrifugation at 6,000 rpm for 10 min, the lipid fractions were extracted in 2 ml of a chloroform-methanol mixture (2:1) at 4° C. overnight, filtered by filter papers, and dried under a nitrogen gas stream. The lipid samples were dissolved in 4 ml of a chloroform-methanol mixture (2:1) and to this solution 1 ml of water was added according to the method of Folch et al. (J. Biol. Chem. 226:497, 1957, which is incorporated herein by reference). The lower phase of the resultant mixture was dried by a nitrogen gas stream and treated with 1 ml of 0.5 N NaOH in methanol at 50° C. for 1 hour. After neutralization with 6 N HCl, 1 ml of petroleum ether was added to the reaction tubes.

After removal of the upper phase, 2 ml of petroleum ether was further added to the lower phase. The dried lower phase was dissolved in 1 ml of a chloroform-methanol-water (86:14:1) mixture (TLP), and then 0.5 ml of another chloroform-methanol-water (3:48:47) mixture (TUP) was added in the same reaction tubes. Finally, the recovered lower phase was dried by a nitrogen gas stream and dissolved in 50 μl of chloroform. One μl of the samples was then added to 1 μl of 2,5-dihydroxybenzoic acid or 1 μl of trans-3-indole acrylic acid used as matrix. Mass spectra of the CGL in positive or negative ion mode were taken by a Voyager-DE STR Biospectrometry Workstation (PE Applied Biosystems; Foster City Calif.) of DE MALDI-TOF MS in a reflector mode with laser intensity of 2,300 as described previously (Taketomi and Sugiyama, Meth. Enzymol. 312:80, 2000, which is incorporated herein by reference). A two-point external calibration was performed where phosphatidic acid, that is endogenously expressed in H. pylori (Inamoto et al., supra, 1993), was used an internal standard.

In Vitro Synthesis of CGL by Sonicated H. Pylori

In vitro synthesis of CGL was assayed as described previously with modifications (Warnecke et al., J. Biol. Chem. 274:13048, 1999, which is incorporated herein by reference). Briefly, H. pylori was precultured in Brucella broth supplemented with 10% horse serum. The diluted bacteria at $5\times10^7$ cells/ml were cultured in Brucella broth supplemented with 5% horse serum at 35° C. for 2 days. Two ml of H. pylori ($5\times10^8$ cells/ml) were centrifuged at 6,000 rpm for 10 min and washed in PBS ($Ca^{2+}$, $Mg^{2+}$ free) three times. H. pylori was then suspended in 1 ml of reaction buffer containing 100 mM Tris buffer (pH 7.5), 15% glycerol, 5 mM DTT, 200 TM PEFABLOC protease inhibitor (Merck, KGaA, Darmstadt, Germany), and 0.5 mg/ml of lysozyme and incubated for 5 min at 20° C. These samples were placed on ice and sonicated 10 times for 30 sec in a ultrasonic water bath with 30 sec-intervals.

One hundred μl of reaction mixture containing 80 μl of the sonicated H. pylori, 5 μl of 8 mM cholesterol in ethanol, and 5 μl of 7.2 μM UDP-glucose, 1 μl of CF-54, and 9 μl of reaction buffer or the same buffer containing 5.0 mU of soluble CD43 with terminal α1,4-linked GlcNAc or the same protein concentration of soluble CD43 without terminal α1,4-linked GlcNAc were incubated at 30° C. for 3 hours. The reaction was terminated by adding 900 μl of a 0.45% NaCl solution and then 4 ml of a chloroform-methanol mixture (2:1). The lower phase of the resultant mixtures was filtered and dried under a nitrogen gas stream. Then, the samples were sequentially treated in a manner similar to that described above. Mass spectra of the CGL in positive ion mode was taken by a Voyager-DE STR Biospectrometry Workstation (Applied Biosystems) of DE MALDI-TOF MS in a reflector mode with a laser intensity of 2,500 as described previously (Taketomi and Sugiyama, supra, 2000). A two-point external calibration was performed.

Cultivation of H. Pylori in the Presence or Absence of Cholesterol

H. pylori was precultured in Brucella broth supplemented with 10% horse serum. Diluted bacteria ($1\times10^8$ cells/ml) were cultured in Brucella broth supplemented with 5% horse serum for 40 hours, then $1\times10^7$ cells of H. pylori were cultured in horse serum-depleted Brucella broth (for TLC analysis) or F-12 medium (for cell growth assay) containing 0.005% cholesterol or lacking cholesterol for 5 to 21 days under standard culture conditions. For culture in F-12 medium, a half volume of the culture medium was carefully removed and replaced by an equal volume of the fresh medium every 2 or 3 days up to 21 days.

Thin-layer Chromatography (TLC)

Glycolipid fractions were extracted from $1\times10^8$ cells of H. pylori using a chloroform-methanol mixture (2:1) at room temperature for 1 hour, dried under a nitrogen gas stream, then subjected to TLC using chloroform-methanol-water (16:6:1) mixture as described (8). Separated glycolipids were visualized by charring with orcinol-containing sulfuric acid buffer at 110° C.

Coculture of H. Pylori with AGS Cells Stably Expressing Terminal α1,4-Linked GlcNAc Gastric adenocarcinoma AGS-α4GnT cells stably expressing terminal α1,4-linked GlcNAc were established as described previously (Nakayama et al., supra, 1999). AGS-I4GnT cells and mock-transfected AGS cells were cocultured with $1\times10^7$ cells/ml of H. pylori (ATCC43504) for 24 hours. After fixation with 20% buffered formalin, cells were incubated with a mixture of rabbit polyclonal antisera against H. pylori (DAKO; Glostrup, Denmark) and mouse monoclonal HIK1083 antibody (Kanto Kagaku; Ishihara et al., supra, 1996). For secondary antibodies, rhodamine-labeled anti-rabbit immunoglobulins (for anti-*H. pylori* antibody) and fluorescein isothiocyanate-labeled anti-mouse IgM (for HIK1083 antibody) were used. Slides were mounted with VECTORSHIELD shielding solution (Vector Laboratories; Burlingame Calif.) and viewed under a laser confocal microscope LSM510 META (Carl Zeiss).

Results

As disclosed herein, a mucin-type glycoprotein containing α1,4-linked GlcNAc was produced to determine its effect on *H. pylori* in culture. As previously shown, CD43 (leukosialin) serves as a preferential core protein of these O-glycans (Nakayama et al., supra, 1999). In order to test the activity of this subset of O-glycans on *H. pylori*, recombinant soluble CD43 having O-glycans with terminal α1,4-linked GlcNAc was generated in Chinese hamster ovary (CHO) cells by transfecting them with cDNAs for α1,4-N-acetylglucosaminyltransferase (α4GnT; Nakayama et al., supra, 1999), core2 β1,6-N-acetylglucosaminyltransferase-I (C2GnT-I; Bierhuizen and Fukuda, supra, 1992), and soluble CD43. As a control, soluble CD43 without terminal α1,4-linked GlcNAc was produced by transfecting CHO cells in the same manner but without α4GnT cDNA.

*H. pylori* (ATCC43504) was incubated with the medium containing varying amounts of recombinant soluble CD43. Microbes grew very little during the first 2.5 days (FIG. 2A), irrespective of the presence or absence of terminal α1,4-linked GlcNAc, as is characteristic of the lag phase of *H. pylori* growth. After 3 days of cultivation, microbes grew rapidly, corresponding to the log phase. However, the growth rate of *H. pylori* was dramatically suppressed when bacteria were incubated with soluble CD43 containing the terminal α1,4-linked GlcNAc. This suppressive effect was particularly evident when the concentration of soluble CD43 exceeded 62.5 mU/ml (1 mU was equivalent to 1 µg of p-nitrophenyl-N-acetylglucosamine (GlcNAcα-PNP); Warnecke et al., *J. Biol. Chem.* 274:13048, 1999, which is incorporated herein by reference). Furthermore, in the presence of 31.2 mU/ml of soluble CD43 expressing α1,4-linked GlcNAc, time-lapse images revealed significant reduction of motility (FIG. 2B), and electron micrographs showed remarkable morphological abnormalities of *H. pylori*, including elongation, segmental narrowing, and curving (FIG. 2C).

Figure 2:
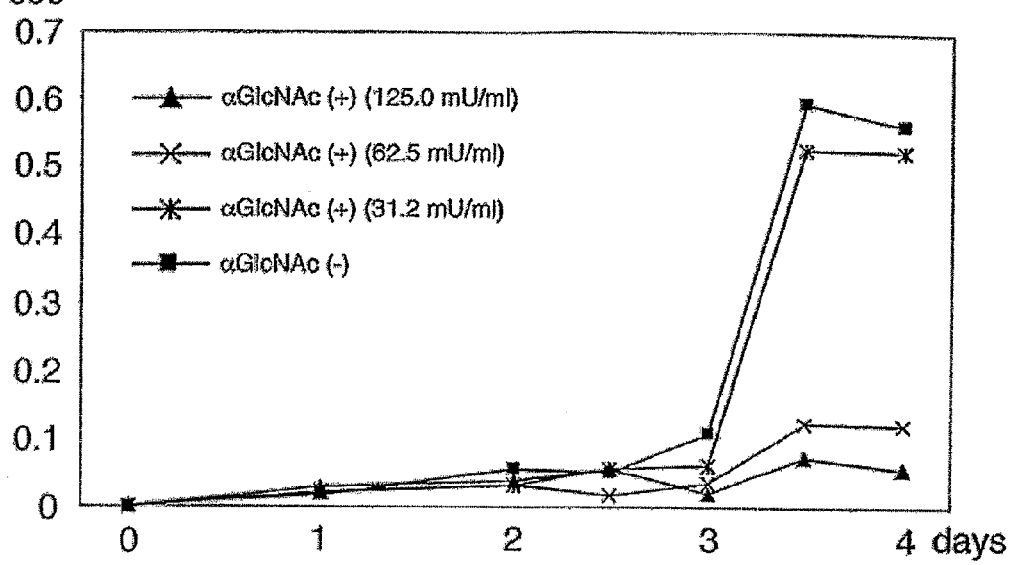
FIGS. 2A to 2C show that O-glycans with terminal α1,4-linked GlcNAc inhibit the growth and motility of *H. pylori*.
Figure 2:
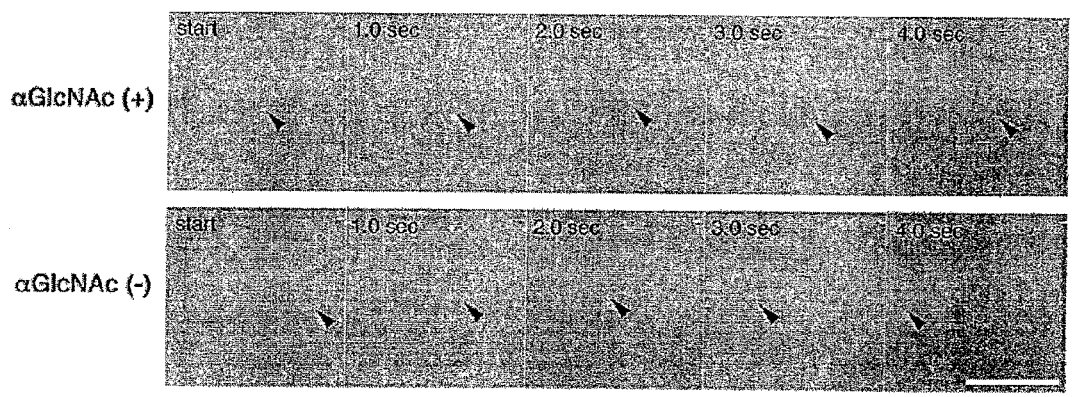
Figure 2:
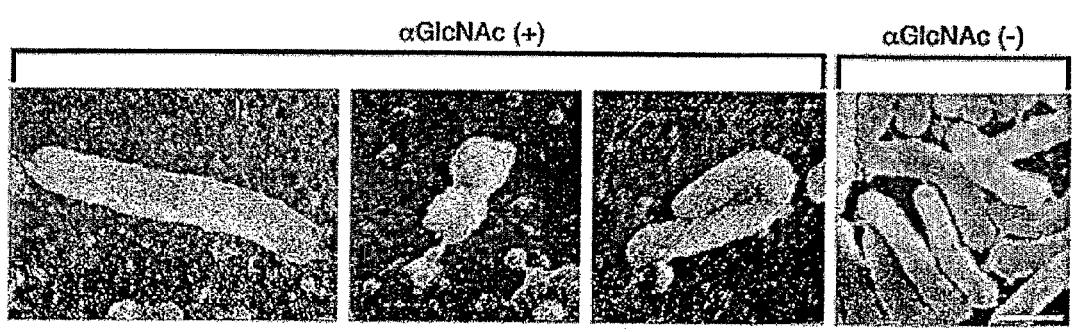

The inhibitory effects of soluble CD43 containing terminal α1,4-linked GlcNAc also was observed in various *H. pylori* strains, including another authentic strain, ATCC43526 and 3 clinical isolates (Warnecke et al., supra, 1999) with a minimum inhibitory concentration between 15.6 mU/ml and 125.0 mU/ml. In contrast, neither an inhibitory growth effect nor abnormal morphology was noted when *H. pylori* was incubated with soluble CD43 lacking the terminal α1,4-linked GlcNAc residues (FIG. 2). These results indicate that O-glycans with terminal α1,4-linked GlcNAc suppress growth of *H. pylori* in a manner similar to antimicrobial agents. Similar inhibitory effects on *H. pylori* also were observed when the terminal α1,4-linked GlcNAc attached to another mucin-like protein, CD34 (Horii et al., *Helicobacter* 7:39, 2002, which is incorporated herein by reference) was used. This result indicates that terminal α1,4-linked GlcNAc residues, rather than scaffold proteins, are required for growth inhibitory activity against *H. pylori*.

The morphological abnormalities seen in *H. pylori* induced by O-glycans with terminal α1,4-linked GlcNAc were similar to those induced by antibiotics such as β-lactamase inhibitors, which disrupt biosynthesis of the peptidoglycan, a major component of the cell wall of many bacteria strains (Finaly et al., *J. Antimicrob. Chemother.* 52:18, 2003, which is incorporated herein by reference; Horii et al., supra, 2002). As such, the ability of these O-glycans to inhibit cell wall biosynthesis in *H. pylori* was examined. The cell wall of *Helicobacter* species characteristically contains α-cholesteryl glucosides (α-CGs), of which the major components are cholesteryl-α-D-glucopyranoside (CGL; Glcα1→cholesterol), cholesteryl-6-O-tetradecanoyl-α-D-glucopyranoside (CAG), and cholesteryl-6-O-phosphatidyl-α-D-glucopyranoside (CPG; Hirai et al., *J. Bacteriol.* 177:5327, 1995; Haque et al., *J. Bacteriol.* 178:2065, 1996, each of which is incorporated herein by reference).

To determine whether O-glycans with terminal α1,4-linked GlcNAc can interfere with CGL biosynthesis in *H. pylori*, the expression levels of CGL in *H. pylori* cultured in the presence of O-glycans were analyzed. Mass spectrometric analysis of the cell wall components from *H. pylori* cultured in the medium containing O-glycans without terminal α1,4-linked GlcNAc showed a clear signal attributable to CGL (FIG. 3A). In contrasts a parallel analysis of *H. pylori* samples cultured in medium containing O-glycans with terminal α1,4-linked GlcNAc demonstrated remarkable reduction of CGL or 29.5% of the control experiment without terminal α1,4-linked GlcNAc (FIG. 3B). These results indicate that O-glycans with terminal α1,4-linked GlcNAc inhibit biosynthesis of CGL in vivo in *H. pylori* cells.

Although the mechanisms underlying formation of the *H. pylori* cell wall, including, for example, the identity of glycosyltransferase(s) involved in the biosynthesis of α-CGs, are not well understood, CGL is likely formed by a UDP-Glc:sterol glucosyltransferase, which transfers glucose (Glc) from UDP-Glc to the C3 position of cholesterol. As such, sonicated *H. pylori* were examined for the expression of UDP-Glc:sterol glucosyltransferase activity and, if found, to determine whether such activity is inhibited by O-glycans containing terminal α1,4-linked GlcNAc. Cholesterol and UDP-Glc were incubated with sonicated *H. pylori*, and the products were analyzed by mass spectrometry. Significant amounts of CGL were detected (FIG. 3C), indicating that sonicated *H. pylori* expressed an enzymatically active UDP-Glc:sterol glucosyltransferase.

When soluble CD43 containing terminal α1,4-linked GlcNAc was added to the assay, production of CGL was suppressed (FIG. 3D), whereas no effect was seen when soluble CD43 without terminal α1,4-linked GlcNAc was added (FIG. 3E). Considering the structural similarity between a-linked GlcNAc present in the gland mucous cell-type mucin and the α-linked Glc present in CGL, these results indicate that the terminal α1,4-linked GlcNAc residue either can compete with UDP-Glc for a donor substrate of the UDP-Glc:sterol glucosyltransferase, or can directly inhibit glycosyltransferase activity through an end-product inhibition mechanism (Nakayama et al., *J. Biol. Chem.* 271:3684, 1996, which is incorporated herein by reference), resulting in decreased CGL biosynthesis.

Cholesterol is a precursor of CGL. However, genes involved in the biosynthesis of cholesterol are not found in the genome database of *H. pylori* (Tomb et al., *Nature* 388:539, 1997; Marais et al., *Microbiol. Mol. Biol. Rev.* 63:642, 1999). Thus, *H. pylori* may not be able to synthesize CGL in the absence of exogenous cholesterol. When *H. pylori* was cultured for 5 days in medium lacking cholesterol, cell growth of the microbes remained at about 50% levels as compared to cultures with cholesterol (see Table 1, below). In cultures without cholesterol, motile microbes were not detected, and abnormal morphology, in particular elongation of *H. pylori* was evident (similar to those shown in FIG. 2C). When *H. pylori* was further cultured without cholesterol for up to 21 days, the microbes died off completely. In contrast, when *H. pylori* was cultured in medium supplemented with cholesterol, the bacteria grew well and there were no signs of abnormality (Table 1). These results indicate that synthesis of CGL using exogenously supplied cholesterol is required for the survival of *H. pylori*.

TABLE 1

Effects of cholesterol depletion on *H. pylori* in culture.

|  | Ham's F-12 with cholesterol | Ham's F-12 without cholesterol | |
| --- | --- | --- | --- |
|  | 5 days | 5 days | 21 days |
| CFU/ml | 1 × 10$^8$ | 5 × 10$^7$ | no growth |
| motility | good | none | not evaluated |
| morphology | normal | abnormal | not evaluated |

A standard strain (ATCC43504) of *H. pylori* (1×10$^7$ cells/ml) was incubated with Ham's F-12 medium supplemented with 0.005% cholesterol for 5 days or without cholesterol up to 21 days at 35° C. in a standard anaerobic condition. CFU; colony forming unit.

To determine the expression levels of CGL in *H. pylori* cultured with or without cholesterol, the expression profile of α-CGs, including CGL in the glycolipid fraction of *H. pylori*, was analyzed by TLC. In *H. pylori* cultured in the presence of cholesterol, a typical triplet of α-CGs including CGL characteristic of *H. pylori* was detected (FIG. 4, lane 2), whereas α-CGs were not detected in *H. pylori* cultured in the absence of cholesterol (FIG. 4, lane 1). Together, these results indicate that CGL is required for *H. pylori* cell growth, and that O-glycans with terminal α1,4-linked GlcNAc have antimicrobial activity against *H. pylori* through inhibition of CGL biosynthesis. In addition, the results suggest that antimicrobial activity of O-glycans with terminal α1,4-linked GlcNAc may be restricted to bacterial strains expressing CGL. In fact, when bacterial strains other than *H. pylori* or strains lacking CGL (e.g., *Escherichia coli, Pseudomonas aeruginosa, Klebsiella pneumoniae, Staphylococcus aureus*, α-*Streptococcus*, and *Streptococcus pneumoniae*) were incubated with soluble CD43 containing terminal α1,4-linked GlcNAc, no antibacterial effect was detected.

The above results indicate that mucous cells expressing O-glycans with terminal α1,4-linked GlcNAc protect themselves against *H. pylori* infection. To confirm this effect, gastric adenocarcinoma AGS-α4GnT cells were stably transfected with α4GnT cDNA (Nakayama et al., supra, 1999) and examined for cellular damage upon *H. pylori* infection. Upon incubation with *H. pylori*, mock-transfected cells exhibited remarkable deterioration such as flatness or shrinkage of cells (see FIG. 5, arrows). In contrast, only a few damaged cells were observed in cultures of AGS-(α4GnT cells with *H. pylori* (FIG. 5). These results confirm that cells expressing mucin-type O-glycans with terminal α1,4-linked GlcNAc are resistant to *H. pylori* infection.

Glycan chains have diverse roles as ligands for cell surface receptors in intercellular interactions (Lowe, *Cell* 104:809, 2001; Akama et al., *Science* 295:124, 2002; Perillo et al., *Nature* 378:736, 1995) and as modulators of receptor and adhesive proteins (Moloney et al., *Nature* 406:369, 2000; Demitriou et al., *Nature* 409:733, 2001; Nakayama et al., *Proc. Natl. Acad. Sci., USA* 92:7031, 1995). The present results have revealed that mammalian glycans also function as a natural antimicrobial agent. Since O-glycans with terminal α1,4-linked GlcNAc are produced by human gastric gland mucous cells, these results provide a basis for developing new therapeutic agents that can prevent and treat *H. pylori* infection in humans without causing adverse reactions.

Although the invention has been described with reference to the above example, it will be understood that modifications and variations are encompassed within the spirit and scope of the invention. Accordingly, the invention is limited only by the following claims.

What is claimed is:

1. An in vitro method of producing a glycoprotein having at least one α1,4-linked N-acetylglucosamine (α1,4-linked GlcNAc) residue, comprising contacting, under conditions suitable for glycosylation of a polypeptide, milk of a mammal containing a carrier polypeptide with an α1,4-N-acetylglucosaminyl transferase (α4GnT), and optionally, a core2 β1,6-N-acetylglucosaminyl transferase-I (C2GnT-I) or a core1 extension β1,3-N-acetylglucosaminyl transferase (C1-β3GnT);

wherein the carrier polypeptide is a mucin-type glycoprotein that includes at least one O-glycosylation site, whereby the carrier polypeptide is glycosylated by the α4GnT, and optionally, by the C2GnT-I or by the C1-β3GnT, thereby producing a glycoprotein having at least one α1,4-linked GlcNAc residue.

2. The method of claim 1, wherein the produced glycoprotein comprises a plurality of α1,4-linked GlcNAc residues.

3. The method of claim 1, further comprising isolating the produced glycoprotein.

* * * * *

SEQUENCE LISTING

```
<160> NUMBER OF SEQ ID NOS: 1

<210> SEQ ID NO 1
<211> LENGTH: 400
<212> TYPE: PRT
<213> ORGANISM: Homo sapiens

<400> SEQUENCE: 1

Met Ala Thr Leu Leu Leu Leu Gly Val Leu Val Val Ser Pro Asp
1               5                   10                  15

Ala Leu Gly Ser Thr Thr Ala Val Gln Thr Pro Thr Ser Gly Glu Pro
            20                  25                  30

Leu Val Ser Thr Ser Glu Pro Leu Ser Ser Lys Met Tyr Thr Thr Ser
        35                  40                  45

Ile Thr Ser Asp Pro Lys Ala Asp Ser Thr Gly Asp Gln Thr Ser Ala
    50                  55                  60

Leu Pro Pro Ser Thr Ser Ile Asn Glu Gly Ser Pro Leu Trp Thr Ser
65                  70                  75                  80

Ile Gly Ala Ser Thr Gly Ser Pro Leu Pro Glu Pro Thr Thr Tyr Gln
                85                  90                  95
```

-continued

```
Glu Val Ser Ile Lys Met Ser Ser Val Pro Gln Glu Thr Pro His Ala
            100             105             110

Thr Ser His Pro Ala Val Pro Ile Thr Ala Asn Ser Leu Gly Ser His
        115             120             125

Thr Val Thr Gly Gly Thr Ile Thr Thr Asn Ser Pro Glu Thr Ser Ser
    130             135             140

Arg Thr Ser Gly Ala Pro Val Thr Thr Ala Ala Ser Ser Leu Glu Thr
145             150             155             160

Ser Arg Gly Thr Ser Gly Pro Pro Leu Thr Met Ala Thr Val Ser Leu
                165             170             175

Glu Thr Ser Lys Gly Thr Ser Gly Pro Pro Val Thr Met Ala Thr Asp
            180             185             190

Ser Leu Glu Thr Ser Thr Gly Thr Thr Gly Pro Pro Val Thr Met Thr
            195             200             205

Thr Gly Ser Leu Glu Pro Ser Ser Gly Ala Ser Gly Pro Gln Val Ser
    210             215             220

Ser Val Lys Leu Ser Thr Met Met Ser Pro Thr Thr Ser Thr Asn Ala
225             230             235             240

Ser Thr Val Pro Phe Arg Asn Pro Asp Glu Asn Ser Arg Gly Met Leu
                245             250             255

Pro Val Ala Val Leu Val Ala Leu Leu Ala Val Ile Val Leu Val Ala
            260             265             270

Leu Leu Leu Leu Trp Arg Arg Gln Lys Arg Arg Thr Gly Ala Leu
            275             280             285

Val Leu Ser Arg Gly Gly Lys Arg Asn Gly Val Val Asp Ala Trp Ala
    290             295             300

Gly Pro Ala Gln Val Pro Glu Glu Gly Ala Val Thr Val Thr Val Gly
305             310             315             320

Gly Ser Gly Gly Asp Lys Gly Ser Gly Phe Pro Asp Gly Glu Gly Ser
            325             330             335

Ser Arg Arg Pro Thr Leu Thr Thr Phe Phe Gly Arg Arg Lys Ser Arg
            340             345             350

Gln Gly Ser Leu Ala Met Glu Glu Leu Lys Ser Gly Ser Gly Pro Ser
        355             360             365

Leu Lys Gly Glu Glu Glu Pro Leu Val Ala Ser Glu Asp Gly Ala Val
    370             375             380

Asp Ala Pro Ala Pro Asp Glu Pro Glu Gly Gly Asp Gly Ala Ala Pro
385             390             395             400
```